(12) United States Patent
Shitagaki et al.

(10) Patent No.: US 7,245,073 B2
(45) Date of Patent: Jul. 17, 2007

(54) QUINOXALINE DERIVATIVES, AND LIGHT EMITTING ELEMENT USING THEREOF

(75) Inventors: Satoko Shitagaki, Kanagawa (JP); Hiroko Abe, Tokyo (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 324 days.

(21) Appl. No.: 10/900,781

(22) Filed: Jul. 28, 2004

(65) Prior Publication Data

US 2005/0065342 A1   Mar. 24, 2005

(30) Foreign Application Priority Data

Jul. 28, 2003 (JP) ............................. 2003-280764

(51) Int. Cl.
*H01J 1/62* (2006.01)
*H01J 63/04* (2006.01)
*C07D 279/18* (2006.01)
*C07D 265/38* (2006.01)
*C07F 5/02* (2006.01)

(52) U.S. Cl. .................. 313/503; 544/34; 544/102; 544/229; 544/353

(58) Field of Classification Search .............. None
See application file for complete search history.

(56) References Cited

U.S. PATENT DOCUMENTS

| | | | |
|---|---|---|---|
| 4,760,006 A | 7/1988 | Pawlowski | 430/78 |
| 5,366,811 A | 11/1994 | Higashi et al. | 428/457 |
| 5,466,392 A | 11/1995 | Hironaka et al. | 252/301.16 |
| 6,541,129 B1 | 4/2003 | Kawamura et al. | |

2003/0143430 A1   7/2003   Kawamura et al.

FOREIGN PATENT DOCUMENTS

| | | |
|---|---|---|
| EP | 0 166 230 | 1/1986 |
| EP | 0 502 202 | 9/1992 |
| JP | 60-258169 | 12/1985 |
| JP | 64-057261 | 3/1989 |
| JP | 07-048385 | 2/1995 |
| JP | 07-150137 | 6/1995 |
| JP | 08-073443 | 3/1996 |
| JP | 10-025473 | 1/1998 |
| JP | 2000-309566 | 11/2000 |
| WO | WO 92/05131 | 4/1992 |
| WO | WO 01/41512 | 6/2001 |

OTHER PUBLICATIONS

Hawley's Condensed Chemical Dictionary, 12th ed., Richard J. Lewis, Sr., © 1993 by Van Nostrand Reinhold, p. 594.*
Concise Encyclopedia Chemistry, edited by Drs. Hans-Dieter Jakubke and Hans Jeschkeit, © 1993 by Walter de Gruyter & Co., p. 490.*
McGraw-Hill Dictionary of Chemical Terms, 3rd ed. edited by Sybil P. Parker, © 1984 McGraw-Hill, Inc., p. 200.*
Delvigs, P. "Effects of Multifunctional Crosslinking Agents on the Thermochemical Properties of Polyimide Films" Polymer Engineering and Science, vol. 16(5), pp. 323-326 (May 1976).*
Brock et al, "Synthesis and Characterisation of Porous Particulate Polyimides" Journal of Materials Chemistry, vol. 4(2), pp. 229-236 (1994).*
Thomas, K. et al, "Quinoxalines Incorporating Triarylamines: Potential Electroluminescent Materials with Tunable Emission Characteristics," Chem. Mater, vol. 14, No. 6, pp. 2796-2802 (2002).
Written Opinion re application No. PCT/JP2004/009845, dated Aug. 31, 2004 (with partial English translation).
Chihaya Adachi et al, "Electroluminescence in Organic Films with Three-Layer Structure", Japanese Journal of Applied Physics, 1988. pp. L269-L271, vol. 27. No. 2.
C W Tang et al , "Organic electroluminescent diodes", Appl Phys Lett , Sep. 21, 1987, pp. 913-915. vol. 51, No. 12.
Translation of International Search Report, application No. PCT/JP2004/009845, dated Aug. 31, 2004 (except the front page).

* cited by examiner

*Primary Examiner*—Zachary C Tucker
(74) *Attorney, Agent, or Firm*—Cook, Alex, McFarron, Manzo, Cummings & Mehler, Ltd.

(57) ABSTRACT

It is an object to provide an organic compound that has a bipolar property and also a light emitting property, and further has heat resistance.

A quinoxaline derivative represented by a general formula (1) is provided. In the formula, A represents any one of an alkylene chain, silicon (Si), oxygen (O), nitrogen (N), and sulfur (S). $R^1$ to $R^8$, which may be identical or different, individually represent any one of a lower alkyl group, an aryl group, and a heterocyclic group. $R^9$ to $R^{24}$, which may be identical or different, individually represent any one of a hydrogen atom, a halogen atom, a lower alkyl group, an alkoxy group, an acyl group, a nitro group, a cyano group, an amino group, a dialkylamino group, a diarylamino group, a vinyl group, an aryl group which may have a substituent, and a heterocyclic group

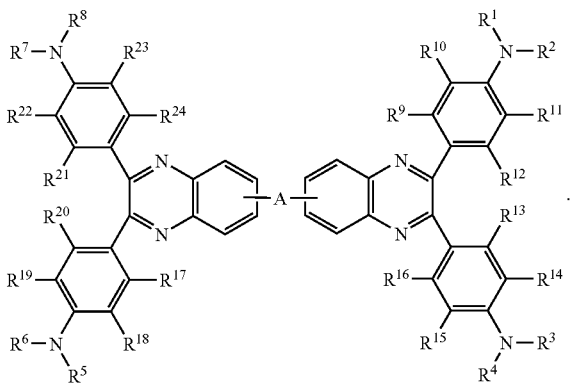

(1)

110 Claims, 8 Drawing Sheets

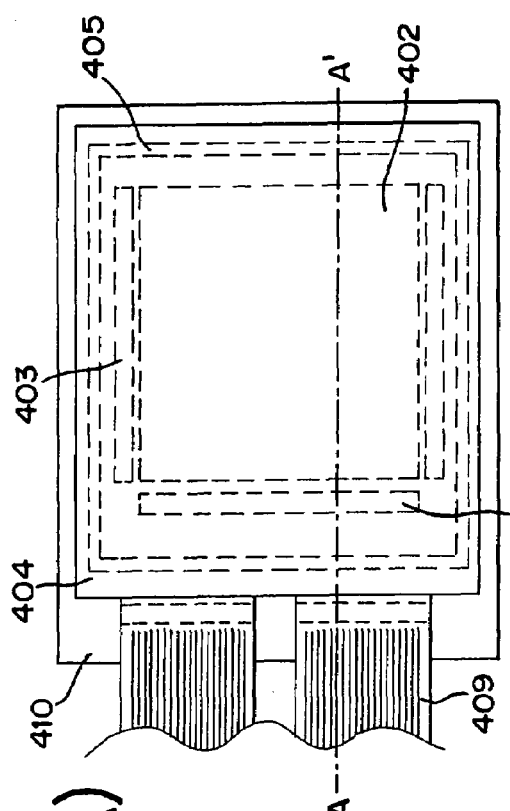
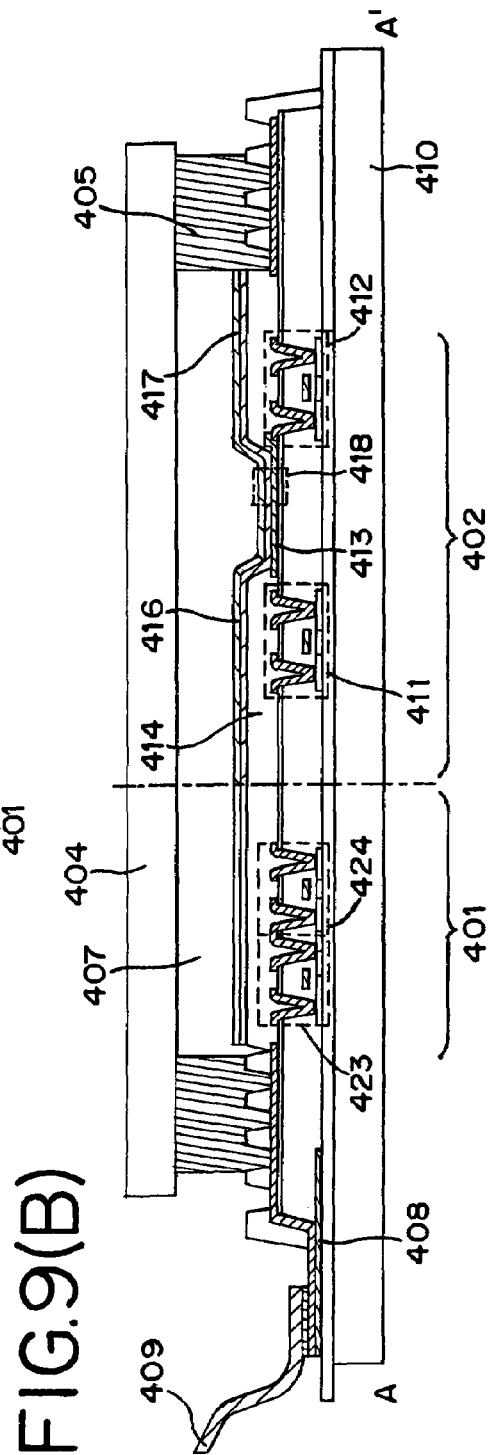
FIG.9(A)
FIG.9(B)

QUINOXALINE DERIVATIVES, AND LIGHT EMITTING ELEMENT USING THEREOF

TECHNICAL FIELD

The present invention relates to a quinoxaline derivative, and also relates to a light-emitting element using the quinoxaline derivative.

BACKGROUND OF THE INVENTION

Organic compounds include more varied materials in comparison with inorganic compounds, and have a possibility that a material that has various functions can be synthesized by an appropriate molecular design. Also, they have features that a molded article such as a film is flexible, and excellent workability is provided by polymerization. Based on these advantages, photonics and electronics using functional organic materials have been attracting attention recently.

For example, examples of an electronic device using an organic compound as a functional organic material include a solar cell, a light-emitting element, and an organic transistor, which are devices utilizing an electric property (carrier transporting property) and an optical property (light absorption or light emission) of the organic compound material, and, among them, the light-emitting element has been showing remarkable progresses.

As a most basic device structure of the light-emitting element, a structure is known, in which a thin film about 100 nm in total, formed by laminating a hole transporting layer comprising a hole transporting organic compound and an electron transporting light-emitting layer comprising an electron transporting organic compound, is interposed between electrodes. By applying a voltage to this element, light emission can be obtained from the electron transporting organic compound that also has a light-emitting property. The structure like this is generally called a single hetero (SH) structure.

It can be said that the light emitting-element in C. W. Tang et al., Applied Physics Letters, Vol. 51, No. 12, 913–915 (1987) is based on a functional separation, namely, transportation of holes being conducted by the hole transporting layer, and transportation of electrons and light emission being conducted by the electron transporting layer Thereafter, for the purposes of further improvement in change in emission spectrum and in decrease in luminous efficiency due to an interaction (for example, formation of exciplex) generated at an interface of laminated layers, the concept of this functional separation has been developed into a concept of a double hetero (DH) structure in which a light-emitting layer is interposed between a hole transporting layer and an electron transporting layer.

In the light-emitting element as described in Chihava Adachi et al., *Japanese Journal of Applied Physics*, Vol. 27, No. 2, L269–L271(1988), in order to further suppress an interaction generated at the interface, it is preferable to use a bipolar material that has both an electron transporting property and a hole transporting property to form the light-emitting layer.

However, many of organic compounds are monopolar materials, which have either a hole transporting property or an electron transporting property. For example, the material shown in Japanese Patent Laid-Open 2003-40873 is only applied as an electron injecting layer.

It is therefore desired to newly develop an organic compound that has a bipolar property.

It is an object of the present invention to provide an organic compound that has a bipolar property and also a light emitting property, and further has heat resistance. It is also an object of the present invention to provide an organic semiconductor device using the organic compound, particularly a light-emitting element that is capable of reducing device defects such as a dielectric breakdown or improving a light emitting property by using the organic compound material.

SUMMARY OF THE INVENTION

The present invention provides a quinoxaline derivative represented by a general formula (1).

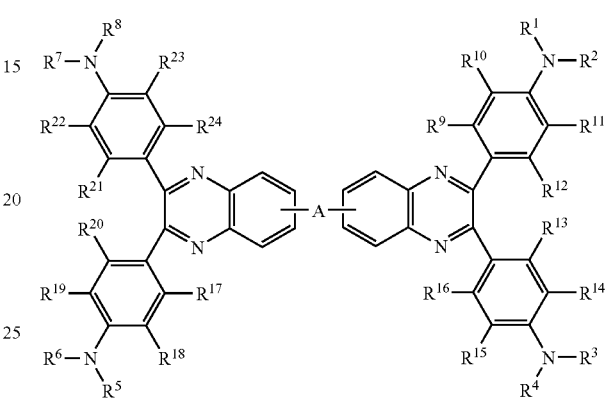

(1)

(In the formula, A represents any one of an alkylene chain, silicon (Si), oxygen (O), nitrogen (N), and sulfur (S). $R^1$ to $R^8$, which may be identical or different, individually represent any one of a lower alkyl group, an aryl group which may have a substituent, and a heterocyclic group which may have a substituent. $R^9$ to $R^{24}$, which may be identical or different, individually represent any one of a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, and a heterocyclic group which may have a substituent.)

The present invention provides a quinoxaline derivative represented by a general formula (2).

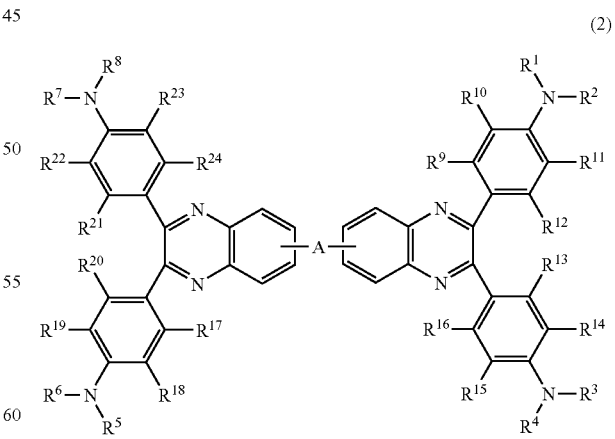

(2)

(In the formula, $R^1$ to $R^8$, which may be identical or different, individually represent any of a lower alkyl group, an aryl group which may have a substituent, and a heterocyclic group which may have a substituent. $R^9$ to $R^{24}$, which may be identical or different, individually represent any one of a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, and a heterocyclic group which may have a substituent.)

The present invention provides a quinoxaline derivative represented by a general formula (3).

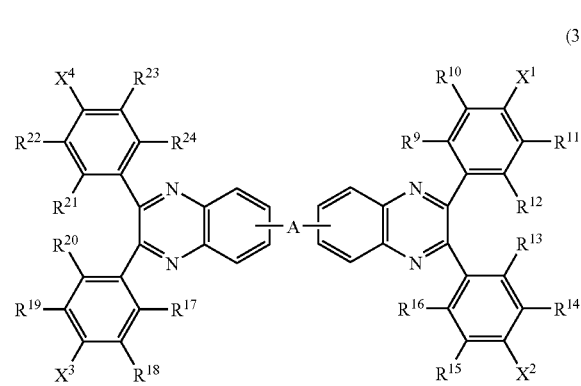

(3)

(In the formula, A represents any one of an alkylene chain, silicon (Si), oxygen (O), nitrogen (N), and sulfur (S). $X^1$ to $X^4$ individually represent any one of general formulas (4) to (6).

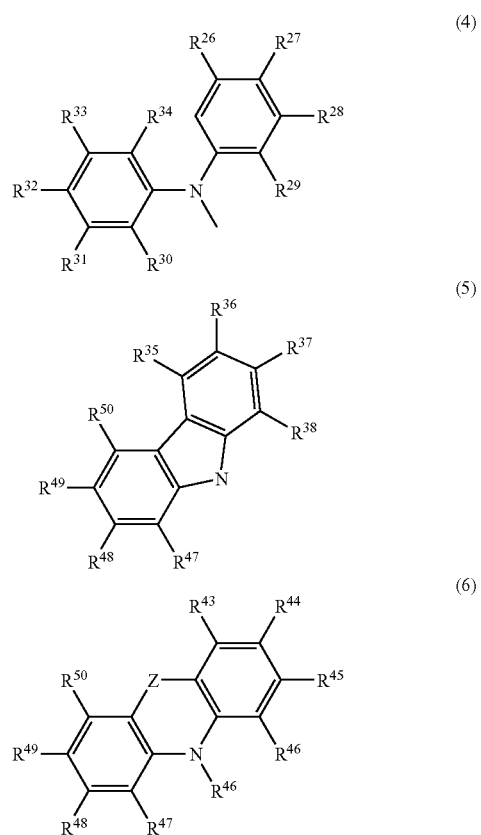

Further, $R^9$ to $R^{50}$, which may be identical or different, individually represent any of a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, and a heterocyclic group which may have a substituent. Z represents any one of oxygen (O), sulfur (S), and a carbonyl group.)

The present invention provides a quinoxaline derivative represented by a general formula (7).

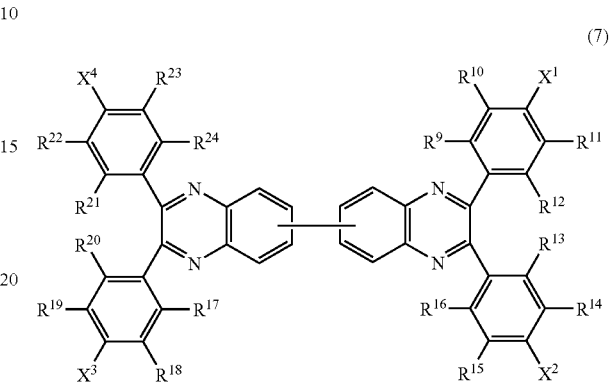

(7)

(In the formula, $X^1$ to $X^4$ individually represent any one of general formulas (4) to (6).

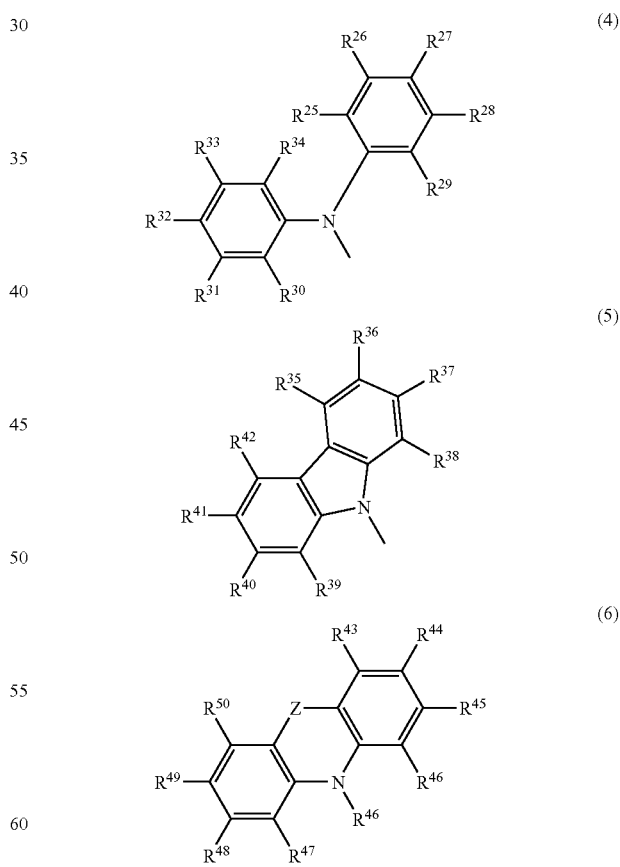

Further, $R^9$ to $R^{50}$, which may be identical or different, individually represent any of a hydrogen atom, a halogen atom, a lower alkyl group, an alkoxy group, an acyl group, a nitro group, a cyano group, an amino group, a dialkylamino group, a diarylamino group, a vinyl group which may have a substituent, an aryl group which may have a substituent, and a heterocyclic group which may have a substituent. Z represents any one of oxygen (O), sulfur (S), and a carbonyl group.)

The present invention provides a quinoxaline derivative represented by a general formula (8).

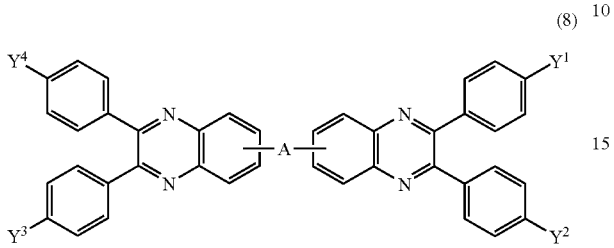
(8)

(In the formula, A represents any one of an alkylene chain, silicon (Si), oxygen (O), nitrogen (N), and sulfur (S). $Y^1$ to $Y^4$ individually represent any one of general formulas (9) to (11).

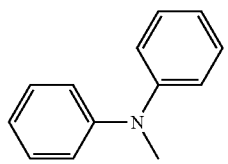
(9)

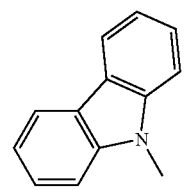
(10)

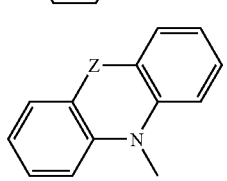
(11)

Z represents any one of oxygen (O), sulfur (S), and a carbonyl group.)

The present invention provides a quinoxaline derivative represented by a general formula (12).

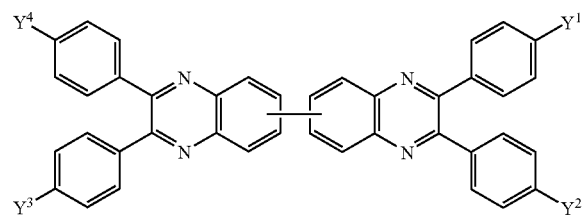
(12)

(In the formula, $Y^1$ to $Y^4$ individually represent any one of general formulas (9) to (11).

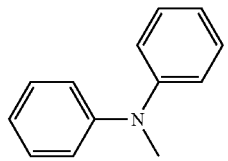
(9)

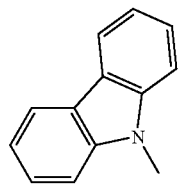
(10)

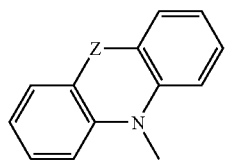
(11)

Z represents any one of oxygen (O), sulfur (S), and a carbonyl group.)

The above-mentioned quinoxaline derivative according to the present invention has a bipolar property and also a light emitting property. Also, a microcrystalline component is not easily included at a film formation by an evaporation method to have a favorable film forming property.

Another structure of the present invention is an organic semiconductor device using the quinoxaline derivative represented by any one of the aforementioned general formulas (1), (2), (3), (7), (8) and (12).

The organic semiconductor device can be, for example, a light-emitting element, an organic transistor, or an organic solar cell.

In addition, the light-emitting element can be a light-emitting element of a structure that has a layer including a luminescent material between a pair of electrodes as a typical example, however, it may be a light-emitting element that has a structure other than this.

The quinoxaline derivative according to the present invention, which has a bipolar property and a light emitting property, can be used for a light-emitting element without particularly including a dopant (guest material). Also, owing to the bipolar property, a light-emitting portion is not easily deviated to an interface of laminated films so that a light-emitting element with a favorable light emitting property can be manufactured with little change in emission spectrum and little decrease in luminous efficiency due to an interaction such as exciplex.

The quinoxaline derivative according to the present invention, which has a light emitting property, can be used for a light-emitting element as a guest material (a light emitter) in combination with a host material.

Also, the quinoxaline derivative according to the invention has a bipolar property, and a microcrystalline component is not easily included at a film formation to have a favorable film forming property. Therefore, the quinoxaline derivative can be used as a host material for a light-emitting layer of a light-emitting element. In the case of using as the host material, it is possible to obtain an emission color due to a guest material, or a mixed emission color of an emission color due to the quinoxaline derivative according to the present invention and an emission color due to the guest material.

Particularly in the case of using the quinoxaline derivative according to the present invention as the host material, a light-emitting element that has a high current efficiency and a low driving voltage can be obtained by using a phosphorescent body which shows light emission from a triplet excited state as a guest material. Therefore, a light-emitting element that has a light-emitting layer including the quinoxaline derivative according to the present invention and a phosphorescent body which shows light emission from a triplet excited state is also included in the present invention. In this case, it is preferable that a peak of an emission spectrum of the phosphorescent body is 560 or more and 700 nm or less.

The present invention allows to obtain a quinoxaline derivative that is an organic compound having a bipolar property and a light emitting property, which further has heat resistance. Also, the use of the quinoxaline derivative according to the invention allows to manufacture a light-emitting element in which a light-emitting portion is not easily deviated to an interface of laminated films, which shows a favorable light emitting property with little change in emission spectrum and little decrease in luminous efficiency due to an interaction such as exciplex. Furthermore, the use of the quinoxaline derivative according to the present invention allows to manufacture a favorable light-emitting element with little device defects such as a dielectric breakdown due to an electric field concentration.

BRIEF DESCRIPTION OF DRAWINGS

FIGS. 9(A)–9(B) are diagrams illustrating a light-emitting device to which the present invention is applied.

DETAILED DESCRIPTION OF THE PRESENTLY PREFERRED EMBODIMENTS (Embodiment 1)

As an embodiment of the present invention, a light-emitting element that is an organic semiconductor device using the quinoxaline derivative according to the present invention will be described with reference to FIG. 1.

Figure 1:
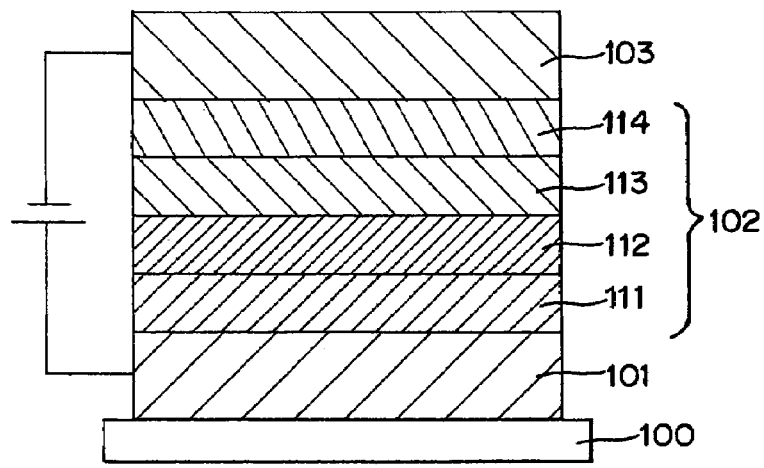
FIG. 1 is a diagram illustrating an embodiment of a light-emitting element according to the present invention.

In FIG. 1, there is a structure in which a first electrode 101 is formed on a substrate 100, a layer 102 including a luminescent material is made on the first electrode 101, and a second electrode 103 is formed thereon.

Here, a material to be used for the substrate 100 can be a material that is used for conventional light-emitting elements, and a substrate comprising a material such as glass, quartz, or transparent plastics, for example, can be used.

In the present embodiment, the first electrode 101 functions as an anode, and the second electrode 103 functions as a cathode.

More specifically, the first electrode 101 is formed of an anode material, and it is preferable to use a metal, an alloy, an electrically conductive compound, and a mixture thereof, which have a large work function (work function of 4.0 eV or more) as the anode material that can be used here. As a specific example of the anode material, it is possible to use gold (Au), platinum (Pt), nickel (Ni), tungsten (W), chromium (Cr), molybdenum (Mo), iron (Fe), cobalt (Co), copper (Cu), palladium (Pd) or a nitride of a metal material (TiN), in addition to indium tin oxide (ITO: Indium Tin Oxide) or indium zinc oxide (IZO: Indium Zinc Oxide) in which indium oxide is mixed with zinc oxide (ZnO) at 2 to 20%.

On the other hand, as the cathode material to be used for forming the second electrode 103, it is preferable to use a metal, an alloy, an electrically conductive compound, and a mixture thereof, which have a small work function (work function of 3.8 eV or less). Specific examples of the cathode material include an element that belongs to group 1 or 2 of the periodic table of the elements, that is, an alkali metal such as lithium (Li) or cesium (Cs), an alkali earth metal such as magnesium (Mg), calcium (Ca) or strontium (Sr), and an alloy including these (Mg:Ag, Al:Li). However, by providing a layer that has a function of promoting electron injection between the second electrode 103 and a light-emitting layer to be laminated with the second electrode 103, it is possible to use various conductive materials such as Al, Ag, and ITO as the second electrode 103 regardless of the magnitude of the work function.

For the layer that has the function of promoting electron injection, a compound of an alkali metal or an alkali earth metal, such as lithium fluoride (LiF), cesium fluoride (CsF) or calcium fluoride ($CaF_2$), can be used. In addition, it is also possible to use a material that has an electron transporting property and include an alkali metal or an alkali earth metal, for example, such as Alq containing magnesium (Mg).

The above-mentioned anode material and cathode material are formed as thin films by a method such as evaporation or sputtering to form the first electrode 101 and the second electrode 103, respectively.

The light-emitting element according to the invention has a structure in which light generated by recombination of carriers in the layer 102 including the luminescent material is emitted to the outside from one of the first electrode 101 and the second electrode 103, or both thereof. Thus, in the case where the light is emitted from the first electrode 101, the first electrode 101 is formed of a light-transmitting material. In the case where the light is emitted from the side of the second electrode 103, the second electrode 103 is formed of a light-transmitting material.

The layer 102 including the luminescent material, which is formed by laminating a plurality of layers, is formed by laminating a hole injecting layer 111, a hole transporting layer 112, a light-emitting layer 113 and an electron transporting layer 114 in the present embodiment.

As a hole injecting material for forming the hole injecting layer 111, phthalocyanine compounds are efficient. For example, phthalocyanine (abbreviation: $H_2Pc$), copper phthalocyanine (abbreviation: CuPc), and the like can be used.

As a hole transporting material for forming the hole transporting layer 112, aromatic amine compounds (that is, compounds that have a benzene ring-nitrogen bond) are suitable. Materials that are widely used include, for example, 4,4'-bis[N-(3-methylphenyl)-N-phenyl-amino]-biphenyl (abbreviation: TPD), and further include derivatives thereof such as 4,4'-bis[N-(1-naphthyl)-N-phenyl-amino]-biphenyl (abbreviation: α-NPD) and starburst aromatic amine compounds such as 4,4',4''-tris(N,N-diphenyl-amino)-triphenylamine (abbreviation: TDATA) and 4,4',4''-tris [N-(3-methylphenyl)-N-phenyl-amino]-triphenylamine (abbreviation: MTDATA).

The light emitting layer 113 is a layer comprising the quinoxaline derivative according to the present invention, which is represented by any one of the general formulas (1), (2), (3), (7), (8), and (12). The quinoxaline derivative according to the present invention, which has a bipolar property and a light emitting property, can be used as the light emitting layer without particularly doping with a guest material that has a light emitting property.

It is believed that the quinoxaline derivative according to the invention have the bipolar property since an electron-donating arylamine skeleton is introduced to a quinoxaline skeleton that has an electron transporting property.

As an electron transporting material in the case of forming the electron transporting layer 114, a metal complex that has a quinoline skeleton or a benzoquinoline skeleton, such as tris(8-quinolinolato) aluminum (abbreviation: $Alq_3$), tris(5-methyl-8-quinolinolato) aluminum (abbreviation: $Almq_3$), bis(10-hydroxybenzo[h]-quinolinato)beryllium (abbreviation: $BeBq_2$), or BAlq mentioned above, is suitable. There are also a metal complex that has an oxazole or thiazole ligand, such as bis[2-(2-hydroxyphenyl)-benzoxazolato] zinc (abbreviation: $Zn(BOX)_2$) or bis[2-(2-hydroxyphenyl-benzothiazolato)zinc (abbreviation: $Zn(BTZ)_2$). In addition to the metal complex, 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproin (abbreviation: BCP), and the like can be used as the electron transporting material.

Based on the foregoing descriptions, the light-emitting element that has the light-emitting layer 113 comprising the quinoxaline derivative according to the present invention, and the hole injecting layer 111, the hole transporting layer 112, and the electron transporting layer 114 comprising the low molecular weight materials can be manufactured. The hole injecting layer 111, the hole transporting layer 112, and the electron transporting layer 114 are not limited to the low molecular materials, and high molecular materials may be used.

The light-emitting element described above emits light by a current flowing due to a potential difference generated between the first electrode 101 and the second electrode 103.

Figure 2:
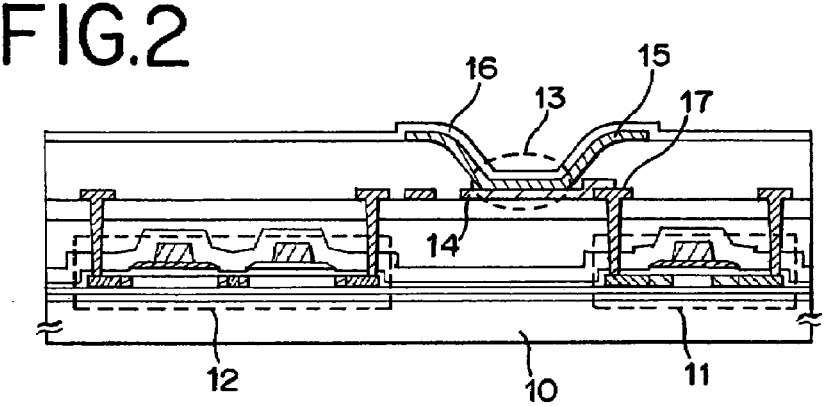
FIG. 2 is a diagram illustrating an embodiment of a light-emitting element according to the present invention.

In the present embodiment, the light-emitting element is manufactured over the substrate 100 comprising a material such as glass, quartz, or transparent plastics. By manufacturing a plurality of light-emitting elements like this over a substrate, a passive light-emitting device can be manufactured. In addition, other than the substrate comprising the material such as glass, quartz, or transparent plastics, for example, as shown in FIG. 2, the light-emitting element may be manufactured over a thin film transistor (TFT) array substrate. This makes it possible to manufacture an active matrix light-emitting device where driving of a light-emitting element is controlled by a TFT. In FIG. 2, TFTs 11 and 12 are provided over a substrate 10. In addition, above the layer where the TFTs 11 and 12 are provided, a light-emitting element 13 that has a layer 15 including a luminescent material between a first electrode 14 and a second electrode 16 is provided, and the first electrode 14 and the TFT 11 are connected through a wiring 17. The structures of the TFTs are not particularly limited.

Further, in the case where it is desired to obtain a multicolor display image by the light-emitting element according to the present invention, a layer including an organic compound according to the present invention as a luminescent material may be formed separately depending on each different emission color by using a mask or a partition layer. In this case, a layer including a luminescent material for displaying each emission color may have a different laminated structure.

In addition, the structure of the layer 102 including the luminescent material is not limited to the above-mentioned structure. A layer including a luminescent material, which has a different laminated structure from the above-mentioned structure, may be employed. For example, layers such as an electron injecting layer, an electron transporting layer, a hole blocking layer, a hole transporting layer, and a hole injecting layer may be freely combined and provided in addition to a light-emitting layer to be a layer including a luminescent material, which has a laminated structure such as a hole injecting layer/a light-emitting layer/an electron transporting layer, a hole injecting layer/a hole transporting layer/a light-emitting layer/an electron transporting layer, a hole injecting layer/a hole transporting layer/a light-emitting layer/an electron transporting layer/an electron injecting layer, a hole injecting layer/a hole transporting layer/a light-emitting layer/a hole blocking layer/an electron transporting layer, or a hole injecting layer/a hole transporting layer/a light-emitting layer/a hole blocking layer/an electron transporting layer/an electron injecting layer. Further, a structure using a single layer of the quinoxaline derivative according to the present invention may be employed since the quinoxaline derivative according to the present invention has a hole transporting property and an electron transporting property, and has a light emitting property.

The quinoxaline derivative according to the present invention, which is a material with a bipolar property and a light emitting property, can be used as a light-emitting layer without including a dopant (a guest material) or the like, as shown in the present embodiment. Also, owing to the bipolar property, a light-emitting portion is not easily deviated to an interface of laminated films so that a light-emitting element with a favorable light emitting property can be manufactured with little change in emission spectrum and little decrease in luminous efficiency due to an interaction such as exciplex. Also, since there is a very little microcrystalline component included in a film formation to provide a favorable film forming property, it is possible to manufacture a favorable light-emitting element with little device defects such as a dielectric breakdown due to an electric field concentration. Also, the quinoxaline derivative according to the present invention, which is a material that has carrier transporting properties (electron transporting property and hole transporting property), can reduce the driving voltage of a light-emitting element by being used for a light-emitting layer.

(Embodiment 2)

In the present embodiment, a light-emitting element using a quinoxaline derivative according to the present invention as a guest material will be described.

The quinoxaline derivative according to the present invention, which has a light emitting property, can be used also as a guest material (a light emitter) for obtaining light emission of a blue to blue-green color.

Also, the quinoxaline derivative according to the present invention, which is a material that has carrier transporting properties, can reduce the driving voltage of the light-emitting element by being used as the guest material.

In this case, an element structure that has a layer including a luminescent material (which may have a structure of single layer or laminated layers) using an organic compound layer including the quinoxaline derivative represented by the general formula (1), (2) or (6) as a light-emitting layer, which is interposed between a pair of electrodes (an anode and a cathode), may be employed. For example, in a light-emitting element that has an element structure such as an anode\a hole injecting layer\a hole transporting layer\a light-emitting layer\an electron transporting layer\a cathode, an anode\a hole injecting layer\a light-emitting layer \an electron transporting layer\a cathode, an anode\a hole injecting layer\a hole transporting layer\a light-emitting layer\an electron transporting layer\an electron injecting layer\a cathode, an anode\a hole injecting layer\a hole transporting layer \a light-emitting layer\a hole blocking layer\an electron transporting layer\a cathode, or an anode\a hole injecting layer\a hole transporting layer\a light-emitting layer\a hole blocking layer\an electron transporting layer\an electron injecting layer\a cathode, a light-emitting layer including the quinoxaline derivative represented by any one of the general formulas (1), (2), (3), (7), (8), and (12) as a guest material can be used.

Here, as the host material, known materials can be used. In addition to the hole transporting materials and electron transporting materials mentioned in Embodiment 1,4,4'-bis (N-carbazolyl)-biphenyl (abbreviation: CBP), 2,2',2"-(1,3,5-benzenetri-yl)-tris[1-phenyl-1H-benzimidazole] (abbreviation: TPBI), 9,10-di(2-naphthyl)anthracene (abbreviation: DNA), and the like can be taken.

In the same way as in shown in Embodiment 1, the light-emitting element described in the present embodiment may be manufactured over a substrate comprising a material such as glass, quartz, or transparent plastics to form a passive light-emitting device or may be manufactured over a TFT array substrate to form an active matrix light-emitting device.

(Embodiment 3)

In the present embodiment, a light-emitting element using a quinoxaline derivative according to the present invention as a host material will be described.

The quinoxaline derivative according to the present invention, which has a bipolar property and has a very little microcrystalline component included in a film formation to provide a favorable film forming property, can be used as a host material.

Also, as described above, the quinoxaline derivative according to the present invention, which is a material that has carrier transporting properties, can reduce the driving voltage of the light-emitting element by being used as the host material.

In case of using as the host material, it is possible to obtain an emission color due to a guest material, or a mixed emission color of an emission color due to the quinoxaline derivative according to the present invention and an emission color due to the guest material with which the quinoxaline derivative is doped.

In this case, an element structure that has a layer including a luminescent material (which may have a structure of single layer or laminated layers) using an organic compound layer including the quinoxaline derivative represented by any one of the general formulas (1), (2), (3), (7), (8), and (12) as a light-emitting layer, which is interposed between a pair of electrodes (an anode and a cathode), may be employed. For example, in a light-emitting element that has an element structure such as an anode\a hole injecting layer\a hole transporting layer\a light-emitting layer\an electron transporting layer\a cathode, an anode\a hole injecting layer\a light-emitting layer\an electron transporting layer\a cathode, an anode\a hole injecting layer\a hole transporting layer\a light-emitting layer\an electron transporting layer\an electron injecting layer\a cathode, an anode\a hole injecting layer\a hole transporting layer\a light-emitting layer\a hole blocking layer\an electron transporting layer\a cathode, or an anode\a hole injecting layer\a hole transporting layer\a light-emitting layer\a hole blocking layer\an electron transporting layer\an electron injecting layer\a cathode, a light-emitting layer including the quinoxaline derivative represented by any one of the general formulas (1), (2), (3), (7), (8), and (12) as a host material can be used.

Here, as the guest material, known materials can be used. Specifically, in addition to fluorescent materials such as 4-(dicyanomethylene)-2-methyl-6-(p-dimethylami-nostyryl)-4H-pyran (abbreviation: DCM1), 4-(dicyanomethylene)-2-methyl-6-(julolidin-4-yl-vinyl)-4H-pyran (abbreviation: DCM2), N,N-dimethylquinacridone (abbreviation: DMQd), 9,10-diphenylanthracene (abbreviation: DPA), 5,12-diphenyltetracene (abbreviation: DPT), coumarine 6, perylene, and rubrene, phosphorescent materials such as bis(2-(2'-benzothienyl)pyridinato-N,$C^3$) (acetylacetonato)iridium (abbreviation: Ir(btp)$_2$(acac)) can be used.

While a light-emitting element obtaining light emission from a triple excited state by adding a phosphorescent material such as the aforementioned iridium complex (for example, Ir(btp)$_2$(acac)) as a guest material has been already known as an element capable of attaining a high efficiency, a high driving voltage has been one of problems conventionally. However, using the quinoxaline derivative according to the present invention as a host material for the phosphorescent material allows to reduce a driving voltage.

In addition, the quinoxaline derivatives of the invention relatively frequently show the light emission in a range of blue to green-yellow color. Therefore, in case of adding a phosphorescent material to the quinoxaline derivative of the invention as a host, the phosphorescent material preferably has a light emitting wavelength at a longer wavelength than in the quinoxaline derivative, particularly in a range of yellow to red color such as about 560 to 700 nm. However such condition is not restrictive as the light emission wavelength of the quinoxaline derivative can be changed by a substituent effect.

In the same way as in shoen in Embodiment 1, the light-emitting element described in the present embodiment may be manufactured over a substrate comprising a material such as glass, quartz, or transparent plastics to form a passive light-emitting device or may be manufactured over a TFT array substrate to form an active matrix light-emitting device.

(Embodiment 4)

In Embodiment 4, an embodiment in which the quinoxaline derivative according to the present invention is used as an active layer of a vertical type transistor (SIT) that is one of organic semiconductor devices will be exemplified.

Figure 3:
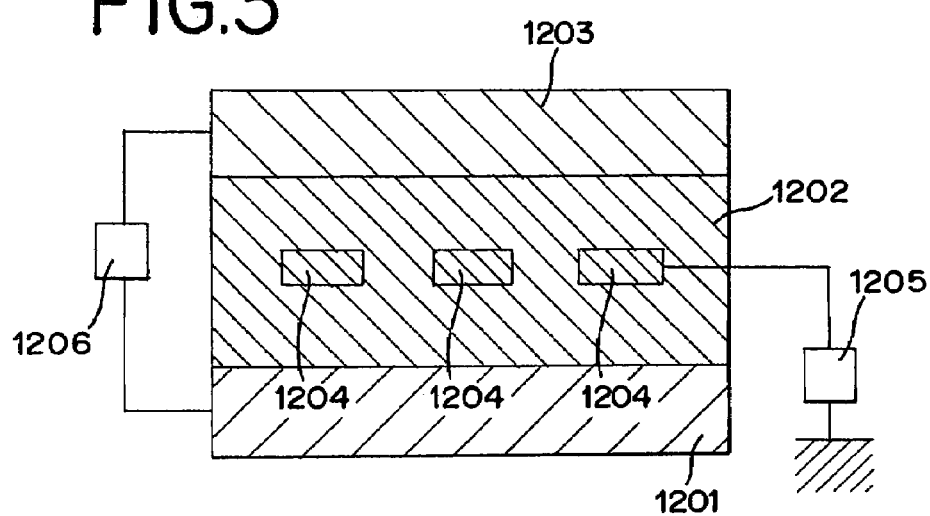
FIG. 3 is a diagram illustrating an embodiment of an organic semiconductor device to which the present invention is applied.

As the structure of the element, a structure is applied, in which, as shown in FIG. 3, a thin film shaped active layer 1202 comprising the quinoxaline derivative according to the present invention is interposed between a source electrode 1201 and a drain electrode 1203, and a gate electrode 1204 is implanted in the active layer 1202. Reference numeral 1205 indicates means for applying a gate voltage, and reference numeral 1206 indicates means for controlling a voltage between the source and the drain.

In the element structure like this, when a voltage is applied between the source and the drain in a state in which a gate voltage is not applied, a current flows as in a light-emitting element (becomes on-state). Then, when a gate voltage is applied in the state, a depletion layer is generated in the vicinity of the gate electrode 1204, whereby no current gets to flows (becomes off-state). Through the above-mentioned mechanisms, a function as a transistor is obained.

In a vertical type transistor, as in a light-emitting element, a material that has both a carrier transporting property and a favorable film forming property is required for an active layer. However, the quinoxaline derivative according to the present invention sufficiently meets the conditions, and is therefore useful.

EXAMPLE 1

Synthesis Example 1

In the present synthesis example, a synthesis method of the quinoxaline derivative according to the present invention, which is represented by the following general formula (13), will be described.

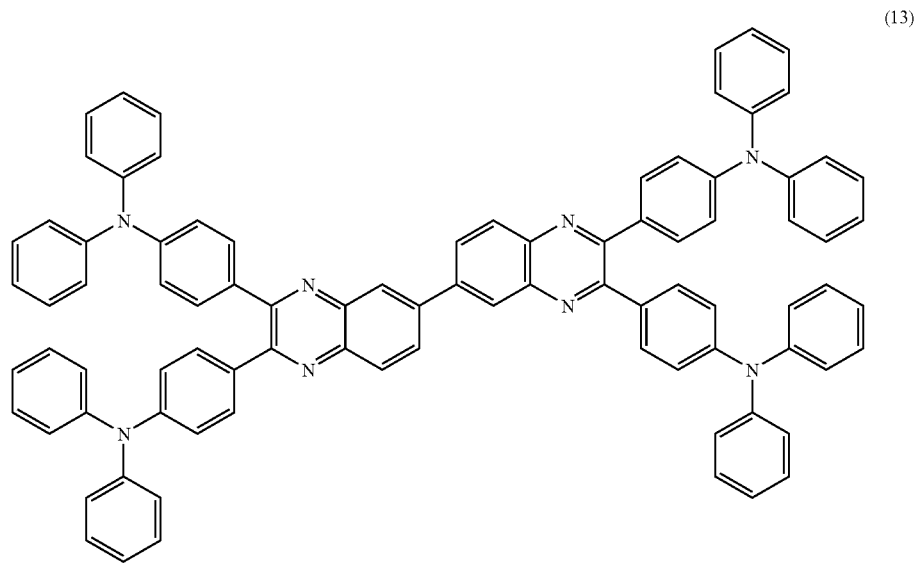

(13)

[Step 1: Synthesis of 2,2',3,3'-tetra(4-bromophenyl)-6,6'-bisquinoxaline]

The present step is represented by the following synthesis scheme (a).

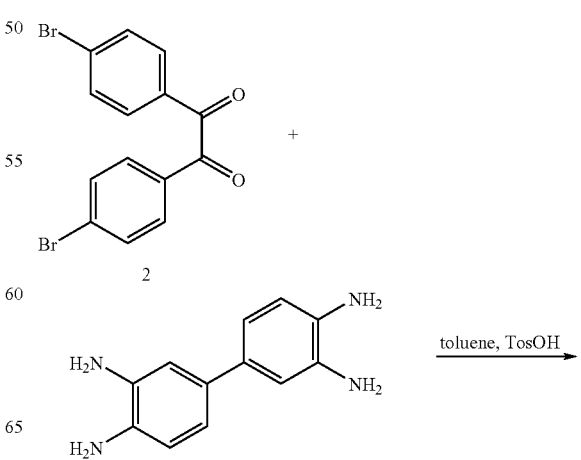

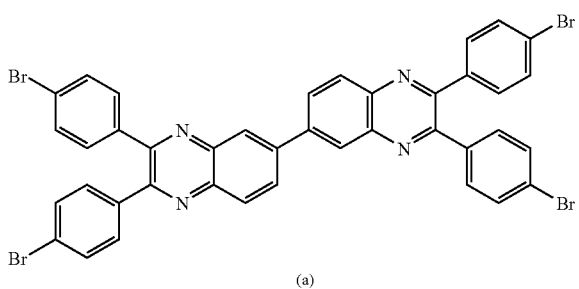

(a)

4-bromobenzyl (7.4 g, 23.0 mmol) and diaminobenzidine (2.4 g, 11.2 mmol) in a 500 ml-recovery-shaped flask equipped with a Dean-Stark tube, to which para-toluenesulfonic acid was added, under a nitrogen flow, were stirred and refluxed in a toluene solvent for 8 hours. TLC was used to confirm that spots of diaminobenzidine disappeared, and the reaction was terminated. After removing the solvent and recrystallizing the obtained precipitation with chloroform (yield: 65% (yield point: 6.29 g)), a measurement by nuclear magnetic resonance (1H-NMR(CDCl3)) provided peaks, σ (ppm)=8.56 (1H), 8.25–8.29 (2H), 7.53–7.55 (4H), and 7.44–7.46 (4H), whereby it was possible to confirm that 2,2',3,3'-tetra(4-bromophenyl)-6,6'-bisquinoxaline was synthesized.

[Step 2: Synthesis of 2,2',3,3'-tetra(4-(diphenylamino)-phenyl)-6,6'-bisquinoxaline (abbreviation: D-TriPhAQn)]

The present step is represented by the following synthesis scheme (b).

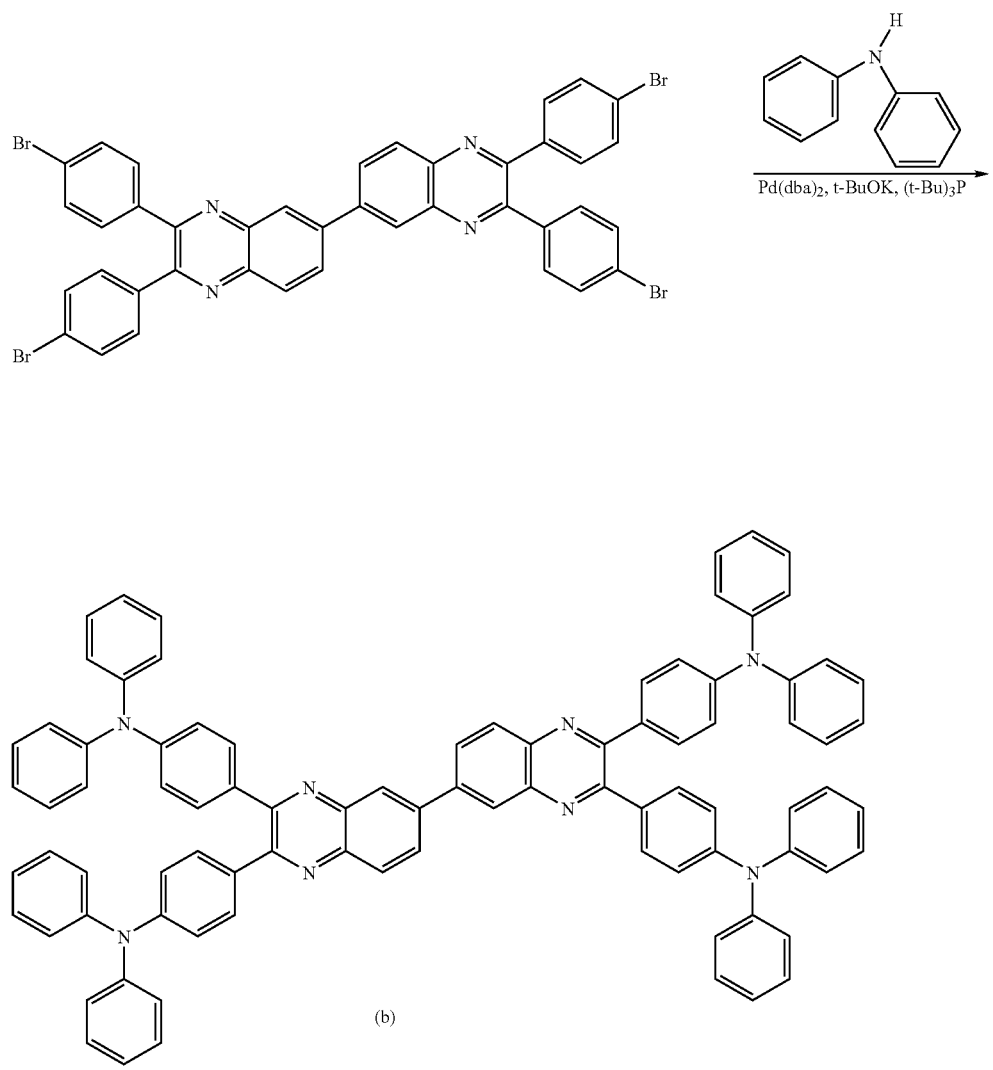

(b)

2,2',3,3'-tetra(4-bromophenyl)-6,6'-bisquinoxaline (2.2 g, 2.5 mmol) synthesized at Step 1 was put in a three-necked flask, and dissolved in 30 ml of toluene under a nitrogen flow, to which Pd(dba)$_2$ (0.22 g, 0.4 mol %%) and NaO-t-Bu (1.44 g, 15 mmol) were added, and further, diphenylamine (1.73 g, 10.2 mmol) and tri (t-butylphosphin) (10 wt % in Hexane) (1.8 mL) were added, and then stirring was performed at 80° C. for 8 hours. After using TLC to confirm that spots of the raw materials disappeared, and cooling to the room temperature, water was added to terminate the reaction. After extracting with chloroform and washing with a saturated salt solution, drying was performed with MgSO$_4$ to yellow-green powder. Yield: 48% (yield point: 1.5 g). A measurement of the obtained yellow-green powder by nuclear magnetic resonance (1H-NMR(CDCl3)) provided peaks, σ (ppm)=8.56 (1H), 8.20–8.29 (2H), 7.33–7.50 (4H), 7.15–7.28 (4H), and 7.04–7.15 (20H), whereby it was possible to confirm that D-TriPhAQn was synthesized.

Figure 4A:
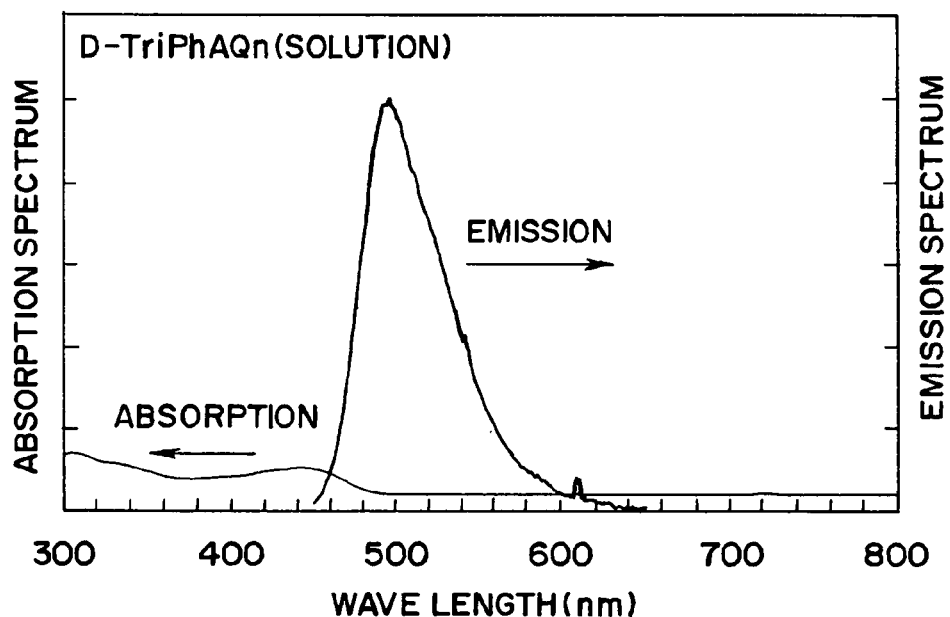
FIGS. 4(A)–4(B) are absorption and emission spectrums of D-TriPhAQn.
Figure 4B:
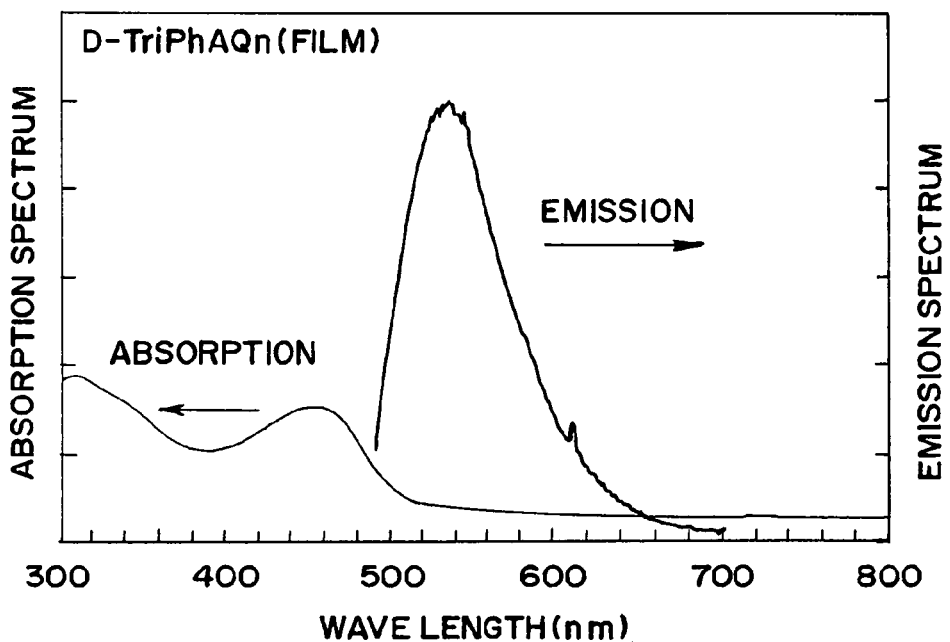

The thus obtained D-TriPhAQn, which lost approximately 10% in weight even when heated to 500° C., showed quite high heat resistance. In addition, absorption and emission spectrums of D-TriPhAQn in a toluene solution and absorption and emission spectrums of a thin film of D-TriPhAQn are shown in FIG. 4(A) and FIG. 4(B), respectively. In the toluene solution, blue-green luminescence with a peak at 500 nm was observed while green luminescence with a peak at 520 nm was observed in the thin film state. In addition, the ionization potential of D-TriPhAQn in a thin film state, measured by photoelectron spectroscopy (AC-2, manufactured by Riken Keiki Co.) in the air, was −5.6 eV. Further, the LUMO level, obtained by using the value of an absorption edge at a longer wavelength side of the absorption spectrum in FIG. 4(B) as an energy gap, was −3.1 eV.

EXAMPLE 2

In the present example, an example of a light-emitting element using a light-emitting layer comprising only the quinoxaline derivative (D-TriPhAQn) according to the present invention, obtained in the foregoing Synthesis Example 1, will be specifically exemplified. The element structure was made similar to that shown in FIG. 1.

At first, a substrate 100 that has ITO deposited as a first electrode 101 on a glass is used. The ITO was made to function as an electrode of a size of 2 mm square. The ITO functions as an anode.

Next, CuPc as a hole injecting layer 111, α-NPD as a hole transporting layer 112, and D-TriPhAQn as a light-emitting layer 113 were deposited to be 20 nm, 30 nm, and 30 nm, respectively. Further, as an electron transporting layer 114, BAlq and Alq were laminated in succession to be 10 nm and 20 nm, respectively. Further, in the present example, after calcium fluoride was laminated on the electron transporting layer 114 to be 2 nm as a layer for promoting electron injection, aluminum (Al) was laminated as a second electrode 103 to obtain a light-emitting element according to the present invention.

Figure 5:
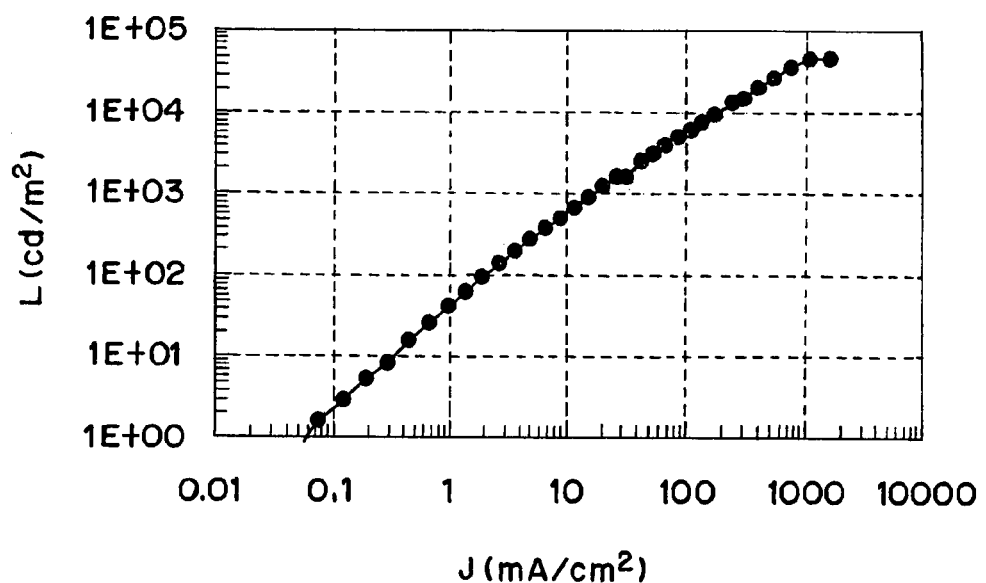
FIG. 5 is a diagram showing luminance-current density (L-J) characteristics of a light-emitting element according to the present invention.
Figure 6:
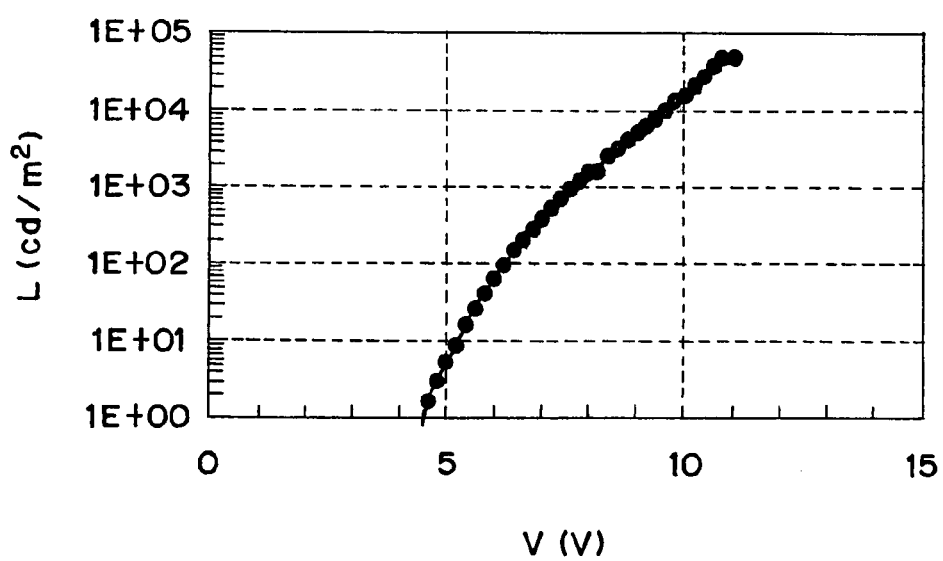
FIG. 6 is a diagram showing luminance-voltage (L-V) characteristics of the light-emitting element according to the present invention.
Figure 7:
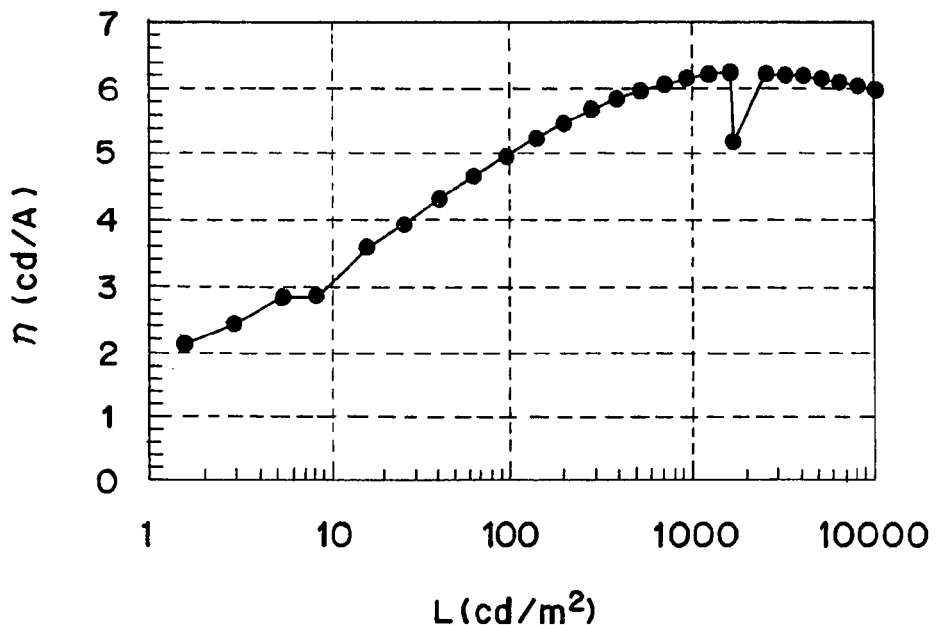
FIG. 7 is a diagram showing current efficiency-luminance (η-L) characteristics of the light-emitting element according to the present invention.

Luminance-current density (L-J) characteristics, luminance-voltage (L-V) characteristics, and current efficiency-luminance (η-L) characteristics of the obtained element are respectively shown in FIGS. 5, 6, and 7. In FIG. 5, the vertical axis and the horizontal axis indicate luminance (cd/m$^2$) and current density (mA/cm$^2$), respectively. Also in FIG. 6, the vertical axis and the horizontal axis indicate luminance (cd/m$^2$) and voltage (V), respectively. Also in FIG. 7, the vertical axis and the horizontal axis indicate current efficiency (cd/A) and luminance (cd/m$^2$), respectively. As for this element, when a voltage of 8V was applied, a current flowed with a current density of 25.2 mA/cm$^2$ and light was emitted with a luminance of 1570 cd/m$^2$. The current efficiency is 6.22 cd/A. The highest luminance reached 50000 cd/m$^2$.

Figure 8:
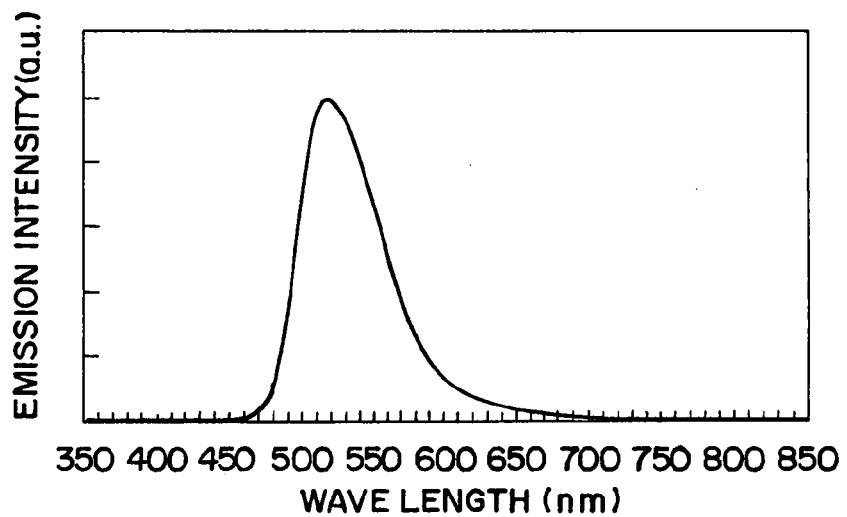
FIG. 8 is a diagram showing an emission spectrum of the light-emitting element according to the present invention.

In addition, the CIE chromaticity coordinates were (x, y)=(0.29, 0.65), and green luminescence was obtained. FIG. 8 shows an emission spectrum of this element. As shown in FIG. 8, the emission spectrum had a peak at about 520 nm.

EXAMPLE 3

Figure 11:
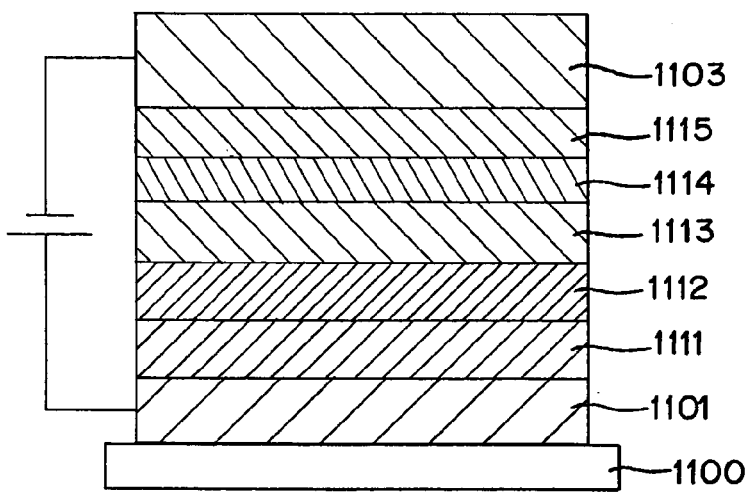
FIG. 11 is a diagram illustrating an embodiment of a light-emitting element according to the present invention.

In the present example, an example of a light-emitting element using the quinoxaline derivative (D-TriPhAQn) according to the present invention, obtained in the foregoing Synthesis Example 1, as a host material of a light-emitting layer will be specifically exemplified. In particular, an element using a phosphorescent material that shows light emission from a triplet excited state as a guest material will be exemplified here. The element structure is shown in FIG. 11. The host material is a material to be used for a material capable of showing light emission of a desired emission wavelength with a preferable luminous efficiency, that is, a material to be used for making a guest material in a dispersion state.

At first, a substrate 1100 that has ITO of 110 nm deposited as a first electrode 1101 over a glass is used. The ITO was made to function as an electrode of a size of 2 mm square. The ITO functions as an anode.

Next, CuPc as a hole injecting layer 1111 and α-NPD as a hole transporting layer 1112 were deposited in succession by vacuum deposition to be 20 nm and 30 nm, respectively. Further, so as to include Ir(btp)$_2$(acac) that is a phosphorescent material at 8 wt %, D-TriPhAQn and Ir(btp)$_2$(acac) were co-deposited, and thus a light-emitting layer 1113 was deposited to be 30 nm. In other words, the quinoxaline derivative D-TriPhAQn according to the present invention functions as a host material. Further, BAlq as a hole blocking layer 1114 and Alq as an electron transporting layer 1115 were laminated in succession by vacuum deposition to be 10 nm and 20 nm, respectively. Further, after calcium fluoride was laminated on the electron transporting layer 1115 to be 2 nm as a layer for promoting electron injection, aluminum (Al) was deposited to be 100 nm as a second electrode 1103 to obtain a light-emitting element according to the present invention.

Figure 12:
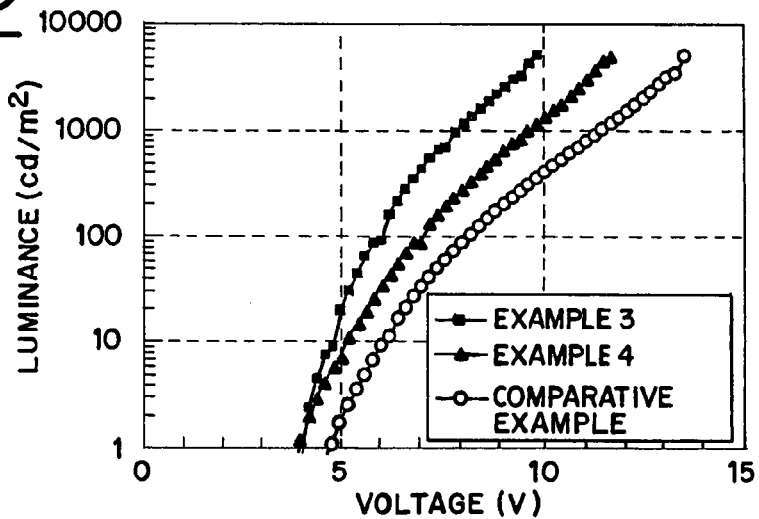
FIG. 12 is a diagram showing voltage-luminance characteristics of light-emitting elements according to the present invention and a light-emitting element according to an comparative example.
Figure 13:
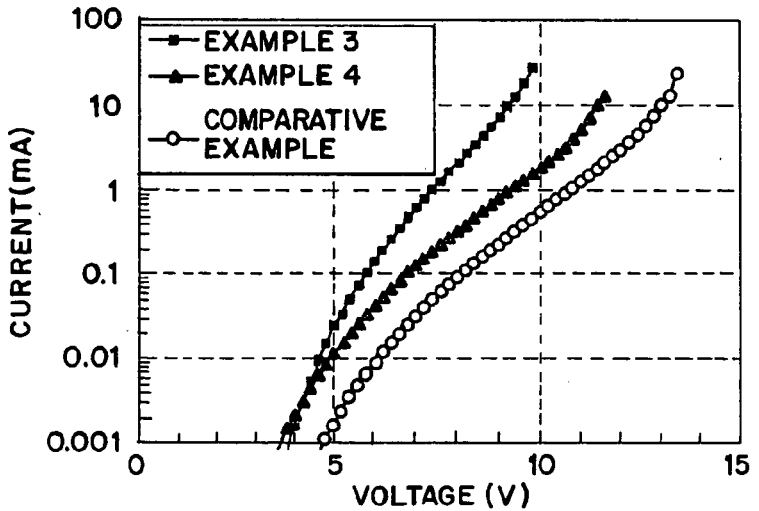
FIG. 13 is a diagram showing voltage-current characteristics of the light-emitting elements according to the present invention and the light-emitting element according to the comparative example.
Figure 14:
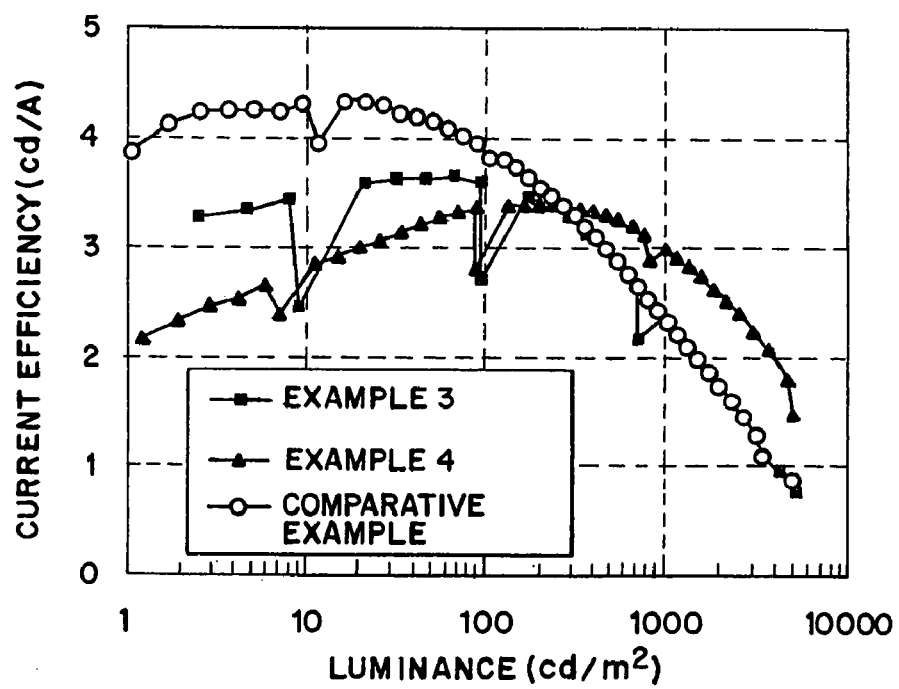
FIG. 14 is a diagram showing luminance-current efficiency characteristics of the light-emitting elements according to the present invention and the light-emitting element according to the comparative example.

Voltage-luminance characteristics, voltage-current characteristics, and luminance-current efficiency characteristics of the obtained element are respectively shown as "Example 3" (■) in FIGS. 12, 13, and 14. In FIG. 12, the vertical axis and the horizontal axis indicate luminance (cd/m$^2$) and voltage (V), respectively. Also in FIG. 13, the vertical axis and the horizontal axis indicate current (mA) and voltage (V), respectively. Also in FIG. 14, the vertical axis and the horizontal axis indicate current efficiency (cd/A) and luminance (cd/m$^2$), respectively. When this element emitted light with a luminance of 450 cd/m$^2$, the driving voltage was 7.0 V, and the current density of a current flowing at this time was 14.9 mA/cm$^2$. The current efficiency is 3.0 cd/A.

Figure 15:
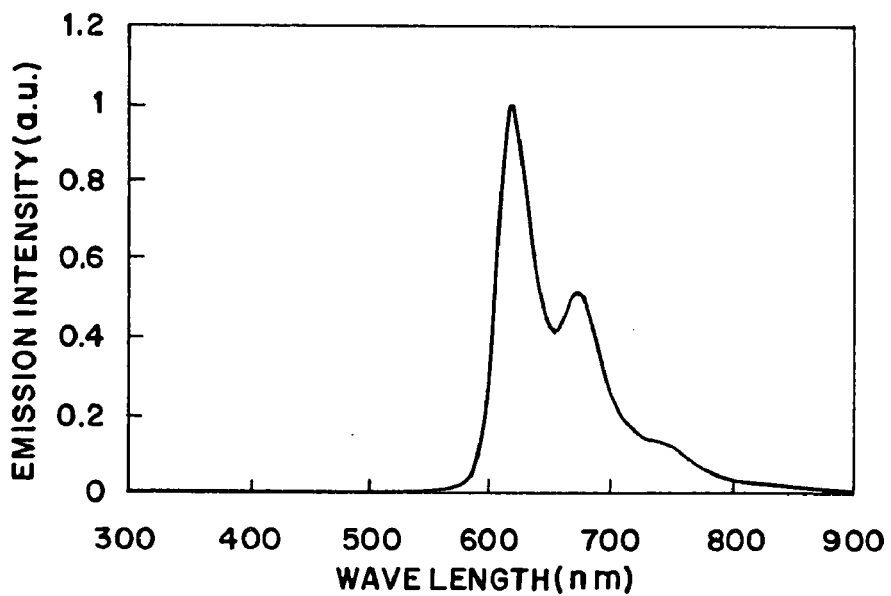
FIG. 15 is a diagram showing an emission spectrum of the light-emitting element according to the present invention.

In addition, an emission spectrum of this element is shown in FIG. 15. It was determined that the shape of the spectrum indicated light emission form Ir(btp)$_2$(acac) that is the phosphorescent material. The CIE chromaticity coordinates were (x, y)=(0.68, 0.31), and red luminescence with favorable chromaticity was obtained.

As mentioned above, the current efficiency is 3.0 cd/A at 450 cd/m$^2$, which means a quite high-efficiency element as a red light-emitting element could be achieved. The high efficiency like this is a feature of an element utilizing a phosphorescent material, and the element of the present example fully exploits the feature. Accordingly, the quinoxaline derivative according to the present invention is appropriate as a host material in a light-emitting layer using a phosphorescent material.

Comparative Example

Results of examining characteristics of a conventional light-emitting element using $Ir(btp)_2(acac)$ as a guest material will be described. The element structure was similar to that in Example 3, except for materials to be the light-emitting layer 1113 and hole blocking layer 1114, and the film thickness of the respective layers were made to be the same. The light-emitting layer 1113 had a conventional structure with CBP as a host material, and the addition concentration of $Ir(btp)_2(acac)$ was made to be 8 wt %. In addition, as the hole blocking layer 1114, BCP was used as conventionally.

Voltage-luminance characteristics, voltage-current characteristics, and luminance-current efficiency characteristics of the obtained element are respectively shown as "Comparative Example" (○) in FIGS. 12, 13, and 14. When this element emitted light with a luminance of 470 $cd/m^2$, the driving voltage was 10.2 V, and the current density of a current flowing at this time was 15.6 $mA/cm^2$. The current efficiency is 3.0 cd/A.

In addition, the shape of an emission spectrum of this element was about the same as in FIG. 15. The CIE chromaticity coordinates were (x, y)=(0.67, 0.31).

In comparison with Example 3, the emission spectrum and the chromaticity are about the same, and the current efficiency is also almost equal. However, as shown in FIG. 12, the driving voltage is found to be larger. Specifically, the voltage necessary for obtaining 50 $cd/m^2$ is approximately 3 V higher. Accordingly, it was determined that the use of the quinoxaline derivative according to the present invention as a host material of a light-emitting layer using a phosphorescent material can reduce driving voltage without damaging an emission color or a luminous efficiency.

In addition, as is clear from FIG. 13, Example 3 shows a shift of the voltage-current characteristics to a lower voltage side as compared with Comparative Example, which indicates a current easily flows. From this point of view, it is believed that, since the quinoxaline derivative according to the present invention is superior to CBP in carrier transporting property, the driving voltage could be reduced. As just described, the quinoxaline derivative according to the present invention has an excellent carrier transporting property. Therefore, the driving voltage can be reduced similarly also in the case of being employed as a host material for other various guet materials.

Based on the foregoing, it was determined that the use of the quinoxaline derivative according to the present invention as a host material in a light-emitting layer can reduce a driving voltage. It was determined that a light-emitting element can be achieved with a higher efficiency and a lower driving voltage than ever before, especially by using as a host material of a phosphorescent material.

EXAMPLE 4

In the present example, an example of a light-emitting element using the quinoxaline derivative (D-TriPhAQn) according to the present invention, obtained in the foregoing Synthesis Example 1, as a host material of a light-emitting layer will be specifically exemplified. In particular, an element using a phosphorescent material that shows light emission from a triplet excited state as a guest material will be exemplified here. The element structure is different from that of Example 3, which is a structure using no hole blocking layer, and is a similar structure to FIG. 1. Therefore, FIG. 1 will be cited below to give an explanation.

At first, a substrate 100 that has ITO of 110 nm deposited as a first electrode 101 on a glass is used. The ITO was made to function as an electrode of a size of 2 mm square. The ITO functions as an anode.

Next, CuPc as a hole injecting layer 111 and α-NPD as a hole transporting layer 112 were deposited by vacuum deposition to be 20 nm and 40 nm, respectively. Further, so as to include $Ir(btp)_2(acac)$ at about 8 wt %, D-TriPhAQn and $Ir(btp)_2(acac)$ were co-deposited, and thus a light-emitting layer 113 was deposited to be 50 nm. In other words, the quinoxaline derivative D-TriPhAQn according to the present invention functions as a host material. Further, Alq as an electron transporting layer 114 was deposited to be 30 nm. Further, after calcium fluoride was laminated on the electron transporting layer 114 to be 2 nm as a layer for promoting electron injection, aluminum (Al) was deposited to be 100 nm as a second electrode 103 to obtain a light-emitting element according to the present invention.

Voltage-luminance characteristics, voltage-current characteristics, and luminance-current efficiency characteristics of the obtained element are respectively shown as "Example 4" (▲) in FIGS. 12, 13, and 14. When this element emitted light with a luminance of 470 $cd/m^2$, the driving voltage was 8.6 V, and the current density of a current flowing at this time was 14.1 $mA/cm^2$. The current efficiency is 3.3 cd/A.

In addition, the shape of an emission spectrum of this element was about the same as in FIG. 15. The CIE chromaticity coordinates were (x, y)=(0.66, 0.33), and red luminescence with favorable chromaticity was obtained.

The current efficiency was almost equal to that of the conventional element (the foregoing comparative example), which means a quite high-efficiency element as a red light-emitting element could be achieved. In addition, it is determined that, even though the element of the present Example 4 has a thicker film thickness than that of the comparative example (140 nm in the present Example 4 while the film thickness of the layer including the luminescent material is 110 nm in the comparative example), the driving voltage is lower as shown in FIG. 12. Specifically, the voltage necessary for obtaining 50 $cd/m^2$ is approximately 1.5 V lower than that in the comparative example. The voltage-current characteristics of FIG. 13 shows a shift to a lower voltage side as compared with the comparative example, from which it is believed that the high carrier transporting property of the quinoxaline derivative according to the present invention contributes to reduction in the driving voltage.

Example 3 and 4 and Comparative Example described above proves that the phosphorescent material emits light with lower power consumption than the light-emitting element using the existing host material (Comparative Example) by using the quinoxaline derivative according to the present invention as the host material in any case of the light-emitting element with the hole blocking layer provided and the light-emitting element with no hole blocking layer provided.

Here, the hole blocking layer is a layer that can prevent a hole from passing from the light-emitting layer to the cathode side and can prevent transfer of excitation energy from the light-emitting layer to the other layer. The hole blocking layer that has the function like this is formed by using a material capable of keeping holes or excitons in, for example, such as BAlq or BCP.

Then, since transfer of holes or transfer of excitation energy can be prevented by providing the hole blocking layer, the phosphorescent material is allowed to emit light with a high current efficiency.

By the way, since crystallization of the layer for forming the light-emitting element contribute to degradation of the element, it is preferable to use a material that is unlikely to undergo crystallization to form the layer. However, many of materials that are appropriate for forming the hole blocking layer are likely to undergo crystallization. Consequently, in the case where it is difficult to select a material that can prevent transfer of holes or transfer of excitation energy and is unlikely to undergo crystallization, it is preferable to use the quinoxaline derivative according to the present invention as a host material to manufacture a light-emitting element without providing a hole blocking layer. This is because the use of the quinoxaline derivative according to the present invention as a host material allows a phosphorescent material to emit light efficiently without particularly providing a hole blocking layer. More specifically, the use of the quinoxaline derivative according to the present invention as a host material makes it possible to obtain a light-emitting element that is not degraded due to crystallization of a hole blocking layer, in which a phosphorescent material emits light with a high current efficiency.

Further, the results of Examples 3 and 4 indicate that the efficiency of energy transfer from the quinoxaline derivative according to the invention to the phosphorescent material is extremely favorable. Also from this point of view, the quinoxaline derivative according to the present invention is found to be suitable as a host material in a light-emitting layer using a phosphorescent material.

EXAMPLE 5

In the present example, a light-emitting device that has a light-emitting element according to the present invention in a pixel portion will be described with reference to FIG. 9. FIG. 9(A) is a top view showing the light-emitting device and FIG. 9(B) is a cross-sectional view taken along line A–A' in FIG. 9(A). Reference numeral 401 indicated by a dotted line denotes a driver circuit portion (a source side driver circuit), reference numeral 402 denotes a pixel portion, and reference numeral 403 denotes a driver circuit portion (a gate side driver circuit). In addition, reference numerals 404 denotes a sealing substrate and 405 denotes a sealing material. The inside surrounded by the sealing material 405 is a space 407.

Reference numeral 408 denotes a wiring for transmitting signals to be input to the source side driver circuit 401 and the gate side driver circuit 403, and receives signals such as a video signal, a clock signal, a start signal, and a reset signal from FPC (Flexible Printed Circuit) 409 that serves as an external input terminal. Though only the FPC is shown in the figure here, a printed wiring board (PWB) may be attached to this FPC. The light-emitting device in the present example includes not only a light-emitting device body but also a state where an FPC or a PWB is attached thereto.

Next, the sectional structure will be explained with reference to FIG. 9(B). The driver circuits and the pixel portion are formed over a substrate 410. Here, the source side driver circuit 401 as the driver circuit portion and the pixel portion 402 are shown.

In the source side driver circuit 401, a CMOS circuit which is a combination of an n-channel TFT 423 and a p-channel TFT 424 is formed. The TFTs forming the driver circuit may be formed of a known CMOS circuit, PMOS circuit, or NMOS circuit. Although the present embodiment shows a driver integrated type in which a driver circuit is formed over a substrate, which is not always necessary, the driver circuit can be formed not over the substrate but outside the substrate.

The pixel portion 402 has a plurality of pixels, each including a switching TFF 411, a current controlling TFT 412, and a first electrode 413 electrically connected to a drain thereof. In addition, an insulator 414 is formed to cover an edge of the first electrode 413. Here, a positive photosensitive acrylic resin film is used to form the insulator 414.

Besides, in order to obtain a favorable coverage, the insulator 414 is made to have a curved surface with a curvature in its top portion or bottom potion. For example, in the case of using positive photosensitive acrylic as a material for the insulator 414, it is preferable that only a top portion of the insulator 414 has a curved surface with a curvature radius (0.2 µm to 3 µm). In addition, both a negative type material that becomes insoluble in an etchant by light and a positive type material that becomes soluble in an etchant by light can be used as the insulator 414.

On the first electrode 413, a layer 416 including a luminescent material and a second electrode 417 are formed. Here, as a material to be used for the first electrode 413 that functions as an anode, it is preferable to use a material that has a large work function. For example, in addition to single layers such as an ITO (indium tin oxide) film, an indium zinc oxide (IZO) film, a titanium nitride film, a chromium film, a tungsten film, a Zn film, and a Pt film, a laminate of titanium nitride and a film including aluminum as its main component, a three-layer structure of a titanium nitride film, a film including aluminum as its main component, and a titanium nitride film, and the like can be used. When a laminated structure is employed, the wiring has a lower resistance, favorable ohmic contact can be taken, and it is possible to function as an anode.

The layer 416 including the luminescent material is formed by evaporation that uses an evaporation mask or by inkjet. For a portion of the layer 416 including the luminescent material, an organic compound according to the present invention is used. In addition, as materials that can be used for the layer 416 including the luminescent material, a low molecular weight material and a high molecular weight material may be used. Moreover, as a material to be used for the layer 416 including the luminescent material, it is often the case that an organic material is used for a single layer or laminate. However, the present example includes a structure in which an inorganic compound is used for a part of a film including an organic compound.

In the case where it is desired to obtain a multicolor display image, a layer including an organic compound according to the present invention as a luminescent material may be formed separately depending on each different emission color by using a mask or a partition layer. In this case, a layer including a luminescent material for displaying each emission color may have a different laminated structure.

In addition, as a material to be used for the second electrode (cathode) 417 formed on the layer 416 including the luminescent material, a material that has a small work function (Al, Ag, Li, or Ca; an alloy thereof such as MgAg, MgIn, Al—Li, or CaF$_2$; or CaN) may be used. In the case of transmitting light generated in the layer 416 including the luminescent material through the second electrode 417, it is preferable to use a laminate of a metal thin film that has a thinned film thickness and a transparent conductive film (such as ITO (indium tin oxide), an alloy of indium oxide and zinc oxide (In$_2$O$_3$—ZnO), or zinc oxide (ZnO)), as the second electrode (cathode) 417.

Further, the sealing substrate 404 and the element substrate 410 are bonded with the sealing material 405 to have a structure where a light-emitting element 418 is provided in the space 407 surrounded by the element substrate 410, the sealing substrate 404, and the sealing material 405. The space 407 also includes a structure of filling with the sealing material 405 in addition to a case of filling with an inert gas (such as nitrogen or argon).

It is preferable to use an epoxy resin for the sealing material 405. In addition, it is desirable to use a material that allows permeation of moisture or oxygen as little as possible. Further, as a material to be used for the sealing substrate 404, a plastic substrate including FRP (Fiberglass-Reinforced Plastics), PVF (polyvinylfluoride), Mylar, polyester, or acrylic can be used besides a glass substrate and a quarts substrate.

In this way, the light-emitting device that has the light-emitting element according to the present invention can be obtained.

EXAMPLE 6

In the present example, electronic devices to which the present invention is applied will be described with reference to FIG. 10. By applying the present invention, a light-emitting element that has a low driving voltage can be provided. Therefore, in an electronic device in which a light-emitting element according to the present invention is mounted, the power consumption can be reduced.

Figure 10A:
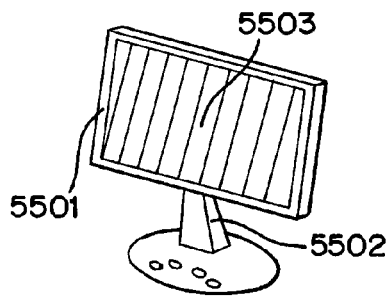
FIGS. 10(A)–10(F) are diagrams illustrating electronic devices to which the present invention is applied.

FIG. 10(A) is a display device, which includes a frame body 5501, a support 5502, and a display portion 5503. A display device can be completed by incorporating the light-emitting device shown in Example 3 in the display device.

Figure 10B:
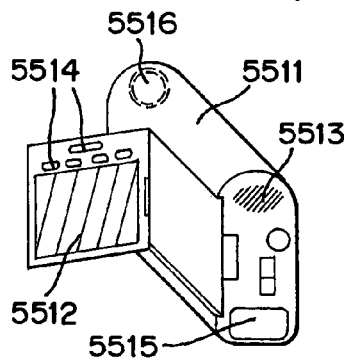

FIG. 10(B) is a video camera, which includes a main body 5511, a display portion 5512, a voice input 5513, operation switches 5514, a battery 5515, and an image receiving portion 5516. A display device can be completed by incorporating the light-emitting device shown in Example 3 in the video camera.

Figure 10C:
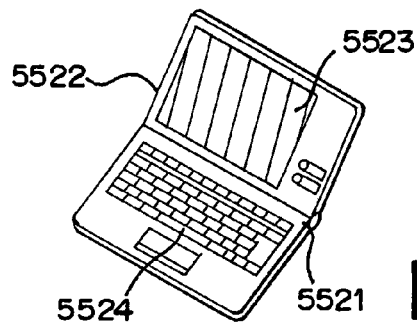

FIG. 10(C) is a laptop personal computer manufactured by applying the present invention, which includes a main body 5521, a frame body 5522, a display portion 5523, and a keyboard 5524. A display device can be completed by incorporating the light-emitting device shown in Example 3 in the laptop personal computer.

Figure 10D:
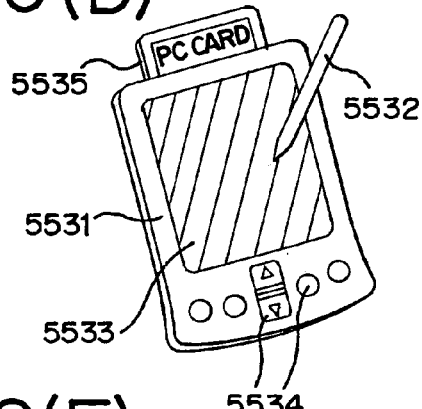

FIG. 10(D) is a personal digital assistant (PDA) manufactured by applying the present invention, which includes a main body 5531 provided with a display portion 5533, an external interface 5535, operation buttons 5534, and the like. As an attachment for operations, a stylus 5532 is provided. A display device can be completed by incorporating the light-emitting device shown in Example 3 in the personal digital assistant (PDA).

Figure 10E:
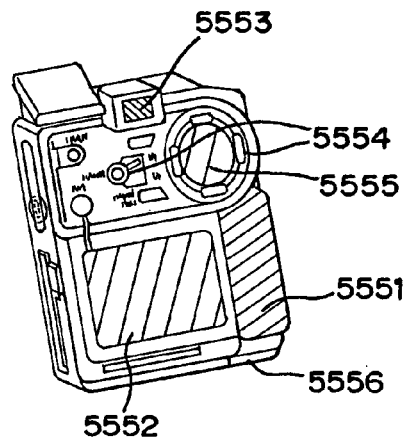

FIG. 10(E) is a digital camera, which includes a main body 5551, a display portion (A) 5552, an eye piece 5553, operation switches 5554, a display portion (B) 5555, and a battery 5556. A display device can be completed by incorporating the light-emitting device shown in Example 3 in the digital camera.

Figure 10F:
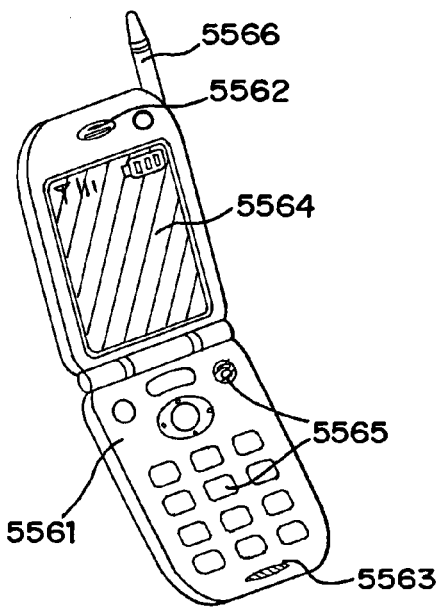

FIG. 10(F) is a cellular phone manufactured by applying the present invention, which includes a main body 5561 provided with a display portion 5564, a voice output portion 5562, operation switches 5565, an antenna 5566, and the like. A display device can be completed by incorporating the light-emitting device shown in Example 3 in the cellular phone.

The invention claimed is:

1. A quinoxaline derivative represented by the following formula (1):

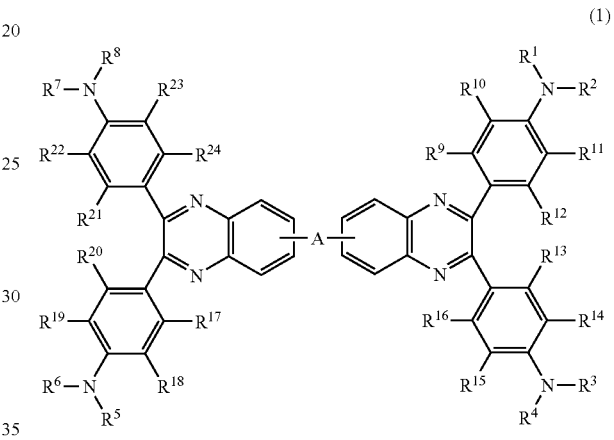

(1)

wherein A represents any one atom of silicon (Si), oxygen (O), nitrogen (N), and sulfur (S), $R^1$ to $R^8$ individually represent any one of a lower alkyl group, an aryl group and a heterocycle group $R^9$ to $R^{24}$ individually represent any one of a hydrogen atom, a halogen atom, a lower alkyl group, an alkoxy group, an acyl group, a nitro group, a cyano group, an amino group, a dialkylamino group, a diarylamino group, a vinyl group, and an aryl group, and a heterocycle group.

2. A quinoxaline derivative represented by the following formula (2):

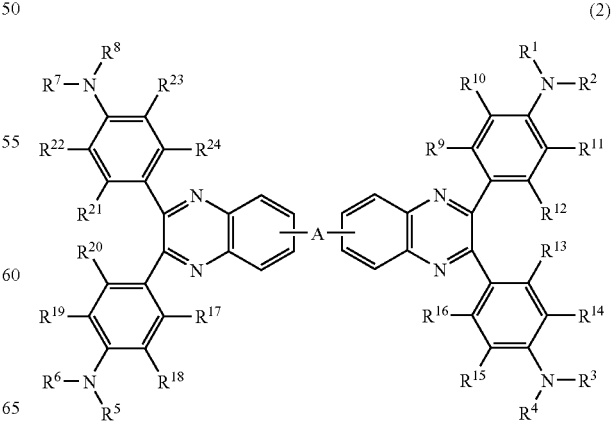

(2)

wherein R¹ to R⁸ individually represent any of a lower alkyl group, an aryl group and a heterocycle group R⁹ to R²⁴ individually represent any one of a hydrogen atom, a halogen atom, a lower alkyl group, an alkoxy group, an acyl group, a nitro group, a cyano group, an amino group, a dialkylamino group, a diarylamino group, a vinyl group, and an aryl group, and a heterocycle group.

3. A quinoxaline derivative represented by the following formula (3):

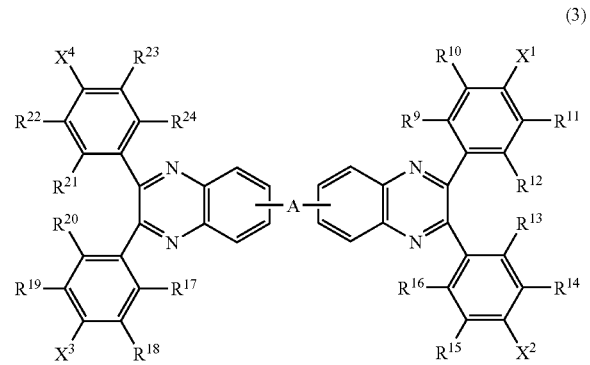

wherein A represents any one atom of silicon (Si), oxygen (O), nitrogen (N), and sulfur (S), $X^1$ to $X^4$ individually represent any one of the following formulas (4) to (6):

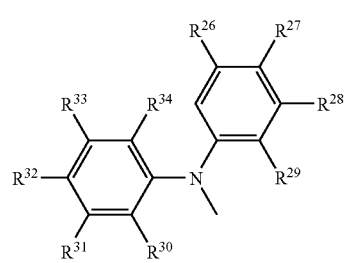

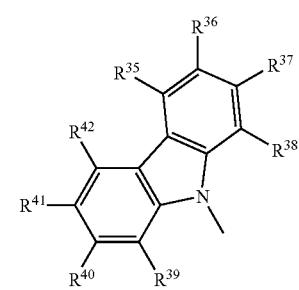

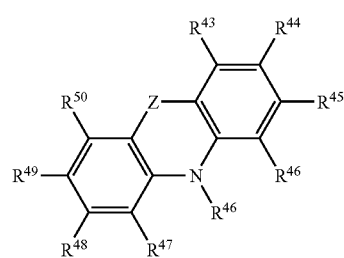

wherein, $R^9$ to $R^{50}$ individually represent any of a hydrogen atom, a halogen atom, a lower alkyl group, an alkoxy group, an acyl group, a nitro group, a cyano group, an amino group, a dialkylamino group, a diarylamino group, a vinyl group, and an aryl group, and a heterocycle group, Z represents any one of oxygen (O), sulfur (S), and a carbonyl group.

4. A quinoxaline derivative represented by the following formula (7):

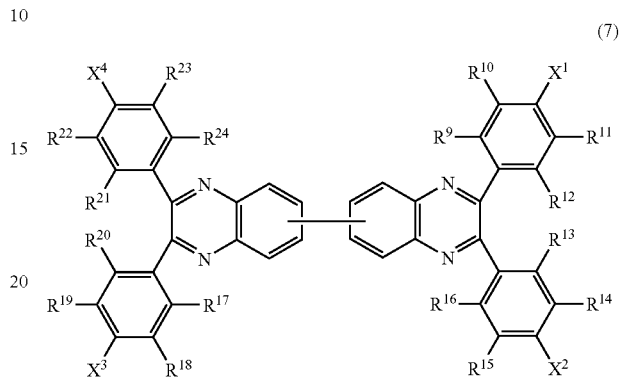

wherein $X^1$ to $X^4$ individually represent any one of the following formulas (4) to (6):

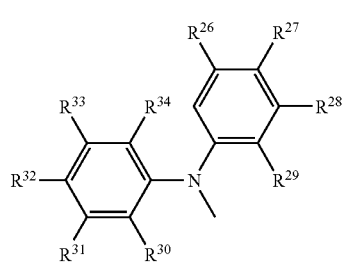

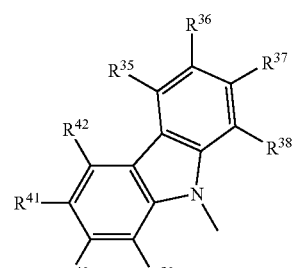

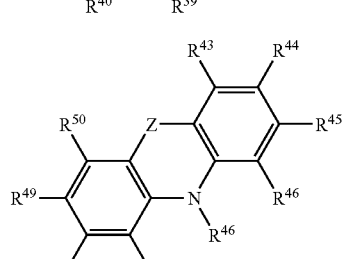

wherein, $R^9$ to $R^{10}$ individually represent any of a hydrogen atom, a halogen atom, a lower alkyl group, an alkoxy group, an acyl group, a nitro group, a cyano group, an amino group, a dialkylamino group, a diarylamino group, a vinyl group, and an aryl group, and a heterocycle group, Z represents any one of oxygen (O), sulfur (S), and a carbonyl group.

5. A quinoxaline derivative represented by the following formula (8):

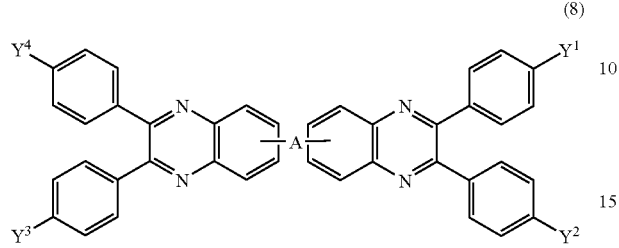

(8)

wherein A represents any one atom of silicon (Si), oxygen (O), nitrogen (N), and sulfur (S), $Y^1$ to $Y^4$ individually represent any one of the following formulas (9) to (11):

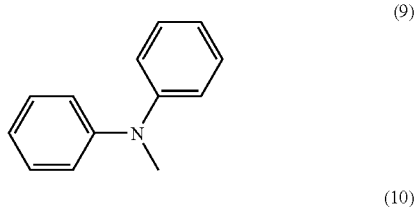

(9)

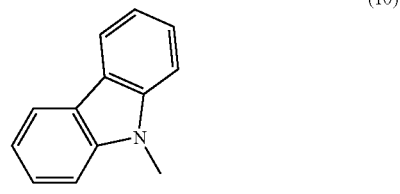

(10)

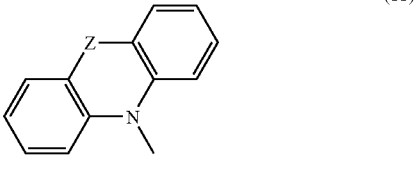

(11)

wherein Z represents any one of oxygen (O), sulfur (S), and a carbonyl group.

6. A quinoxaline derivative represented by the following formula (12):

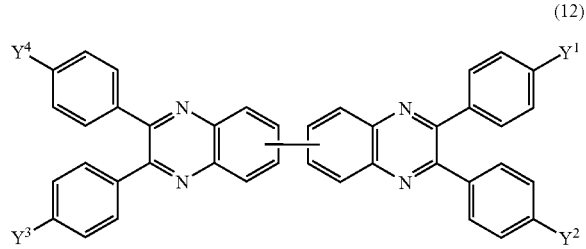

(12)

wherein $Y^1$ to $Y^4$ individually represent any one of the following formulas (9) to (11):

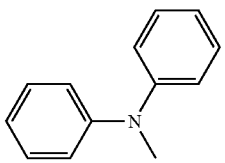

(9)

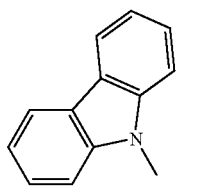

(10)

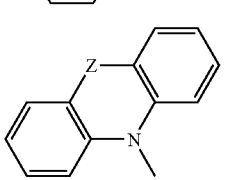

(11)

wherein Z represents any one of oxygen (O), sulfur (S), and a carbonyl group.

7. An organic semiconductor device comprising the quinoxaline derivative according to claim 1.

8. A light-emitting element comprising the quinoxaline derivative according to claim 1.

9. The quinoxaline derivative according to claim 1, wherein the each of $R^1$ to $R^8$ represents an aryl group having a substituent or a heterocycle group having a substituent.

10. The quinoxaline derivative according to claim 2, wherein the each of $R^1$ to $R^8$ represents an aryl group having a substituent or a heterocycle group having a substituent.

11. A light-emitting element comprising a layer including the quinoxaline derivative according to claim 1, wherein the layer is interposed between a pair of electrodes.

12. A light-emitting element comprising the quinoxaline derivative according to claim 1, wherein the quinoxaline derivative is a light emitter.

13. A light-emitting element comprising the quinoxaline derivative according to claim 1, wherein the quinoxaline derivative is a host material.

14. A light-emitting element comprising a layer including the quinoxaline derivative according to claim 1 and a phosphorescent body which shows light emission from a triplet excited state.

15. A light-emitting element comprising a layer including the quinoxaline derivative according to claim 1 and a phosphorescent body which shows light emission from a triplet excited state, wherein the emission spectrum of the phosphorescent body is 560 nm or more and 700 nm or less.

16. A light-emitting device comprising a light-emitting element having a layer including the quinoxaline derivative according to claim 1 between a pair of electrodes, wherein the light-emitting element is included in a pixel portion.

17. A light-emitting device comprising a light-emitting element comprising the quinoxaline derivative according to claim 1 as a light emitter, wherein the light-emitting element is included in a pixel portion.

18. A light-emitting device comprising a light-emitting element comprising the quinoxaline derivative according to claim 1 as a host material, wherein the light-emitting element is included in a pixel portion.

19. A light-emitting device comprising a light-emitting element having a layer including the quinoxaline derivative according to claim 1 and a phosphorescent body which shows light emission from a triplet excited state, wherein the light-emitting element is included in a pixel portion.

20. A light-emitting device comprising a light-emitting element having a layer including the quinoxaline derivative according to claim 1 and a phosphorescent body which shows light emission from a triplet excited state, wherein the emission spectrum of the phosphorescent body is 560 nm or more and 700 nm or less, and wherein the light-emitting element is included in a pixel portion.

21. An electronic device having the light-emitting device according to claim 16 for a display portion, wherein the electronic device is selected from the group consisting of a display device, a camera, a laptop personal computer, a personal digital assistant, and a phone.

22. An electronic device having the light-emitting device according to claim 17 for a display portion, wherein the electronic device is selected from the group consisting of a display device, a camera, a laptop personal computer, a personal digital assistant, and a phone.

23. An electronic device having the light-emitting device according to claim 18 for a display portion, wherein the electronic device is selected from the group consisting of a display device, a camera, a laptop personal computer, a personal digital assistant, and a phone.

24. An electronic device having the light-emitting device according to claim 19 for a display portion, wherein the electronic device is selected from the group consisting of a display device, a camera, a laptop personal computer, a personal digital assistant, and a phone.

25. An electronic device having the light-emitting device according to claim 20 for a display portion, wherein the electronic device is selected from the group consisting of a display device, a camera, a laptop personal computer, a personal digital assistant, and a phone.

26. An organic semiconductor device comprising the quinoxaline derivative according to claim 2.

27. A light-emitting element comprising the quinoxaline derivative according to claim 2.

28. A light-emitting element comprising a layer including the quinoxaline derivative according to claim 2, wherein the layer is interposed between a pair of electrodes.

29. A light-emitting element comprising the quinoxaline derivative according to claim 2, wherein the quinoxaline derivative is a light emitter.

30. A light-emitting element comprising the quinoxaline derivative according to claim 2, wherein the quinoxaline derivative is a host material.

31. A light-emitting element comprising a layer including the quinoxaline derivative according to claim 2 and a phosphorescent body which shows light emission from a triplet excited state.

32. A light-emitting element comprising a layer including the quinoxaline derivative according to claim 2 and a phosphorescent body which shows light emission from a triplet excited state, wherein the emission spectrum of the phosphorescent body is 560 nm or more and 700 nm or less.

33. A light-emitting device comprising a light-emitting element having a layer including the quinoxaline derivative according to claim 2 between a pail of electrodes, wherein the light-emitting element is included in a pixel portion.

34. A light-emitting device comprising a light-emitting element comprising the quinoxaline derivative according to claim 2 as a light emitter, wherein the light-emitting element is included in a pixel portion.

35. A light-emitting device comprising a light-emitting element comprising the quinoxaline derivative according to claim 2 as a host material, wherein the light-emitting element is included in a pixel portion.

36. A light-emitting device comprising a light-emitting element having a layer including the quinoxaline derivative according to claim 2 and a phosphorescent body which shows light emission from a triplet excited state, wherein the light-emitting element is included in a pixel portion.

37. A light-emitting device comprising a light-emitting element having a layer including the quinoxaline derivative according to claim 2 and a phosphorescent body which shows light emission from a triplet excited state, wherein the emission spectrum of the phosphorescent body is 560 nm or more and 700 nm or less, and wherein the light-emitting element is included in a pixel portion.

38. An organic semiconductor device comprising the quinoxaline derivative according to claim 3.

39. A light-emitting element using the quinoxaline derivative according to claim 3.

40. A light-emitting element comprising a layer including the quinoxaline derivative according to claim 3, wherein the layer is interposed between a pair of electrodes.

41. A light-emitting element comprising the quinoxaline derivative according to claim 3, wherein the quinoxaline derivative is a light emitter.

42. A light-emitting element comprising the quinoxaline derivative according to claim 3, wherein the quinoxaline derivative is a host material.

43. A light-emitting element comprising a layer including the quinoxaline derivative according to claim 3 and a phosphorescent body which shows light emission from a triplet excited state.

44. A light-emitting element comprising a layer including the quinoxaline derivative according to claim 3 and a phosphorescent body which shows light emission from a triplet excited state, wherein the emission spectrum of the phosphorescent body is 560 nm or more and 700 nm or less.

45. A light-emitting device comprising a light-emitting element having a layer including the quinoxaline derivative according to claim 3 between a pair of electrodes, wherein the light-emitting element is included in a pixel portion.

46. A light-emitting device comprising a light-emitting element comprising the quinoxaline derivative according to claim 3 as a light emitter, wherein the light-emitting element is included in a pixel portion.

47. A light-emitting device comprising a light-emitting element comprising the quinoxaline derivative according to claim 3 as a host material, wherein the light-emitting element is included in a pixel portion.

48. A light-emitting device comprising a light-emitting element having a layer including the quinoxaline derivative according to claim 3 and a phosphorescent body which shows light emission from a triplet excited state, wherein the light-emitting element is included in a pixel portion.

49. A light-emitting device comprising a light-emitting element having a layer including the quinoxaline derivative according to claim 3 and a phosphorescent body which shows light emission from a triplet excited state, wherein the emission spectrum of the phosphorescent body is 560 nm or more and 700 nm or less, and wherein the light-emitting element is included in a pixel portion.

50. An organic semiconductor device comprising the quinoxaline derivative according to claim 4.

51. A light-emitting element using the quinoxaline derivative according to claim 4.

52. A light-emitting element comprising a layer including the quinoxaline derivative according to claim 4, wherein the layer is interposed between a pair of electrodes.

53. A light-emitting element comprising the quinoxaline derivative according to claim 4, wherein the quinoxaline derivative is a light emitter.

54. A light-emitting element comprising the quinoxaline derivative according to claim 4, wherein the quinoxaline derivative is a host material.

55. A light-emitting element comprising a layer including the quinoxaline derivative according to claim 4 and a phosphorescent body which shows light emission from a triplet excited state.

56. A light-emitting element comprising a layer including the quinoxaline derivative according to claim 4 and a phosphorescent body which shows light emission from a triplet excited state, wherein the emission spectrum of the phosphorescent body is 560 nm or more and 700 nm or less.

57. A light-emitting device comprising a light-emitting element having a layer including the quinoxaline derivative according to claim 4 between a pail of electrodes, wherein the light-emitting element is included in a pixel portion.

58. A light-emitting device comprising a light-emitting element comprising the quinoxaline derivative according to claim 4 as a light emitter, wherein the light-emitting element is included in a pixel portion.

59. A light-emitting device comprising a light-emitting element comprising the quinoxaline derivative according to claim 4 as a host material, wherein the light-emitting element is included in a pixel portion.

60. A light-emitting device comprising a light-emitting element having a layer including the quinoxaline derivative according to claim 4 and a phosphorescent body which shows light emission from a triplet excited state, wherein the light-emitting element is included in a pixel portion.

61. A light-emitting device comprising a light-emitting element having a layer including the quinoxaline derivative according to claim 4 and a phosphorescent body which shows light emission from a triplet excited state, wherein the emission spectrum of the phosphorescent body is 560 nm or more and 700 nm or less, and wherein the light-emitting element is included in a pixel portion.

62. An organic semiconductor device comprising the quinoxaline derivative according to claim 5.

63. A light-emitting element using the quinoxaline derivative according to claim 5.

64. A light-emitting element comprising a layer including the quinoxaline derivative according to claim 5, wherein the layer is interposed between a pair of electrodes.

65. A light-emitting element comprising the quinoxaline derivative according to claim 5, wherein the quinoxaline derivative is a light emitter.

66. A light-emitting element comprising the quinoxaline derivative according to claim 5, wherein the quinoxaline derivative is a host material.

67. A light-emitting element comprising a layer including the quinoxaline derivative according to claim 5 and a phosphorescent body which shows light emission from a triplet excited state.

68. A light-emitting element comprising a layer including the quinoxaline derivative according to claim 5 and a phosphorescent body which shows light emission from a triplet excited state, wherein the emission spectrum of the phosphorescent body is 560 nm or more and 700 nm or less.

69. A light-emitting device comprising a light-emitting element having a layer including the quinoxaline derivative according to claim 5 between a pair of electrodes, wherein the light-emitting element is included in a pixel portion.

70. A light-emitting device comprising a light-emitting element comprising the quinoxaline derivative according to claim 5 as a light emitter, wherein the light-emitting element is included in a pixel portion.

71. A light-emitting device comprising a light-emitting element using the quinoxaline derivative according to claim 5 as a host material, wherein the light-emitting element is included in a pixel portion.

72. A light-emitting device comprising a light-emitting element having a layer including the quinoxaline derivative according to claim 5 and a phosphorescent body which shows light emission from a triplet excited state, wherein the light-emitting element is included in a pixel portion.

73. A light-emitting device comprising a light-emitting element having a layer including the quinoxaline derivative according to claim 5 and a phosphorescent body which shows light emission from a triplet excited state, wherein the emission spectrum of the phosphorescent body is 560 nm or more and 700 nm or less, and wherein the light-emitting element is included in a pixel portion.

74. An organic semiconductor device comprising the quinoxaline derivative according to claim 6.

75. A light-emitting element comprising the quinoxaline derivative according to claim 6.

76. A light-emitting element comprising a layer including the quinoxaline derivative according to claim 6, wherein the layer is interposed between a pair of electrodes.

77. A light-emitting element comprising the quinoxaline derivative according to claim 6, wherein the quinoxaline derivative is a light emitter.

78. A light-emitting element comprising the quinoxaline derivative according to claim 6, wherein the quinoxaline derivative is a host material.

79. A light-emitting element comprising a layer including the quinoxaline derivative according to claim 6 and a phosphorescent body which shows light emission from a triplet excited state.

80. A light-emitting element comprising a layer including the quinoxaline derivative according to claim 6 and a phosphorescent body which shows light emission from a triplet excited state, wherein the emission spectrum of the phosphorescent body is 560 nm or more and 700 nm or less.

81. A light-emitting device comprising a light-emitting element having a layer including the quinoxaline derivative according to claim 6 between a pair of electrodes, wherein the light-emitting element is included in a pixel portion.

82. A light-emitting device comprising a light-emitting element comprising the quinoxaline derivative according to claim 6 as a light emitter, wherein the light-emitting element is included in a pixel portion.

83. A light-emitting device comprising a light-emitting element comprising the quinoxaline derivative according to claim 6 as a host material, wherein the light-emitting element is included in a pixel portion.

84. A light-emitting device comprising a light-emitting element having a layer including the quinoxaline derivative according to claim 6 and a phosphorescent body which shows light emission from a triplet excited state, wherein the light-emitting element is included in a pixel portion.

85. A light-emitting device comprising a light-emitting element having a layer including the quinoxaline derivative according to claim 6 and a phosphorescent body which shows light emission from a triplet excited state, wherein the emission spectrum of the phosphorescent body is 560 nm or more and 700 nm or less, and wherein the light-emitting element is included in a pixel portion.

86. An electronic device having the light-emitting device according to claim 33 for a display portion, wherein the electronic device is selected from the group consisting of a display device, a camera, a laptop personal computer, a personal digital assistant, and a phone.

87. An electronic device having the light-emitting device according to claim 34 for a display portion, wherein the electronic device is selected from the group consisting of a display device, a camera, a laptop personal computer, a personal digital assistant, and a phone.

88. An electronic device having the light-emitting device according to claim 35 for a display portion, wherein the electronic device is selected from the group consisting of a display device, a camera, a laptop personal computer, a personal digital assistant, and a phone.

89. An electronic device having the light-emitting device according to claim 36 for a display portion, wherein the electronic device is selected from the group consisting of a display device, a camera, a laptop personal computer, a personal digital assistant, and a phone.

90. An electronic device having the light-emitting device according to claim 37 for a display portion, wherein the electronic device is selected from the group consisting of a display device, a camera, a laptop personal computer, a personal digital assistant, and a phone.

91. An electronic device having the light-emitting device according to claim 45 for a display portion, wherein the electronic device is selected from the group consisting of a display device, a camera, a laptop personal computer, a personal digital assistant, and a phone.

92. An electronic device having the light-emitting device according to claim 46 for a display portion, wherein the electronic device is selected from the group consisting of a display device, a camera, a laptop personal computer, a personal digital assistant, and a phone.

93. An electronic device having the light-emitting device according to claim 47 for a display portion, wherein the electronic device is selected from the group consisting of a display device, a camera, a laptop personal computer, a personal digital assistant, and a phone.

94. An electronic device having the light-emitting device according to claim 48 for a display portion, wherein the electronic device is selected from the group consisting of a display device, a camera, a laptop personal computer, a personal digital assistant, and a phone.

95. An electronic device having the light-emitting device according to claim 49 for a display portion, wherein the electronic device is selected from the group consisting of a display device, a camera, a laptop personal computer, a personal digital assistant, and a phone.

96. An electronic device having the light-emitting device according to claim 57 for a display portion, wherein the electronic device is selected from the group consisting of a display device, a camera, a laptop personal computer, a personal digital assistant, and a phone.

97. An electronic device having the light-emitting device according to claim 58 for a display portion, wherein the electronic device is selected from the group consisting of a display device, a camera, a laptop personal computer, a personal digital assistant, and a phone.

98. An electronic device having the light-emitting device according to claim 59 for a display portion, wherein the electronic device is selected from the group consisting of a display device, a camera, a laptop personal computer, a personal digital assistant, and a phone.

99. An electronic device having the light-emitting device according to claim 60 for a display portion, wherein the electronic device is selected from the group consisting of a display device, a camera, a laptop personal computer, a personal digital assistant and a phone.

100. An electronic device having the light-emitting device according to claim 61 for a display portion, wherein the electronic device is selected from the group consisting of a display device, a camera, a laptop personal computer, a personal digital assistant, and a phone.

101. An electronic device having the light-emitting device according to claim 69 for a display portion, wherein the electronic device is selected from the group consisting of a display device, a camera, a laptop personal computer, a personal digital assistant, and a phone.

102. An electronic device having the light-emitting device according to claim 70 for a display portion, wherein the electronic device is selected from the group consisting of a display device, a camera, a laptop personal computer, a personal digital assistant, and a phone.

103. An electronic device having the light-emitting device according to claim 71 for a display portion, wherein the electronic device is selected from the group consisting of a display device, a camera, a laptop personal computer, a personal digital assistant, and a phone.

104. An electronic device having the light-emitting device according to claim 72 for a display portion, wherein the electronic device is selected from the group consisting of a display device, a camera, a laptop personal computer, a personal digital assistant, and a phone.

105. An electronic device having the light-emitting device according to claim 73 for a display portion, wherein the electronic device is selected from the group consisting of a display device, a camera, a laptop personal computer, a personal digital assistant, and a phone.

106. An electronic device having the light-emitting device according to claim 81 for a display portion, wherein the electronic device is selected from the group consisting of a display device, a camera, a laptop personal computer, a personal digital assistant, and a phone.

107. An electronic device having the light-emitting device according to claim 82 for a display portion, wherein the electronic device is selected from the group consisting of a display device, a camera, a laptop personal computer, a personal digital assistant, and a phone.

108. An electronic device having the light-emitting device according to claim 83 for a display portion, wherein the electronic device is selected from the group consisting of a display device, a camera, a laptop personal computer, a personal digital assistant, and a phone.

109. An electronic device having the light-emitting device according to claim 84 for a display portion, wherein the electronic device is selected from the group consisting of a display device, a camera, a laptop personal computer, a personal digital assistant, and a phone.

110. An electronic device having the light-emitting device according to claim 85 for a display portion, wherein the electronic device is selected from the group consisting of a display device, a camera, a laptop personal computer, a personal digital assistant, and a phone.

* * * * *